(12) United States Patent
Ueda et al.

(10) Patent No.: US 10,472,665 B2
(45) Date of Patent: Nov. 12, 2019

(54) MEASURING METHOD AND COMPOSITION USING KINASE

(71) Applicant: ASAHI KASEI PHARMA CORPORATION, Chiyoda-ku, Tokyo (JP)

(72) Inventors: Shigeru Ueda, Tokyo (JP); Shinichi Sakasegawa, Tokyo (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 79 days.

(21) Appl. No.: 15/510,059

(22) PCT Filed: Sep. 18, 2015

(86) PCT No.: PCT/JP2015/076639
§ 371 (c)(1),
(2) Date: Mar. 9, 2017

(87) PCT Pub. No.: WO2016/047580
PCT Pub. Date: Mar. 31, 2016

(65) Prior Publication Data
US 2017/0306389 A1    Oct. 26, 2017

(30) Foreign Application Priority Data
Sep. 26, 2014 (JP) ................................ 2014-196720

(51) Int. Cl.
| | | |
|---|---|---|
| C12Q 1/00 | (2006.01) | |
| C12Q 1/50 | (2006.01) | |
| C12Q 1/48 | (2006.01) | |
| C12M 1/34 | (2006.01) | |
| C12Q 1/54 | (2006.01) | |
| C12Q 1/61 | (2006.01) | |
| C12N 9/12 | (2006.01) | |
| C12Q 1/34 | (2006.01) | |

(52) U.S. Cl.
CPC .............. *C12Q 1/485* (2013.01); *C12M 1/34* (2013.01); *C12N 9/12* (2013.01); *C12Q 1/008* (2013.01); *C12Q 1/48* (2013.01); *C12Q 1/50* (2013.01); *C12Q 1/54* (2013.01); *C12Q 1/61* (2013.01); *C12Y 207/01001* (2013.01); *C12Y 207/0103* (2013.01); *C12Y 207/0104* (2013.01); *C12Y 207/01011* (2013.01); *C12Y 207/01147* (2013.01); *C12Y 207/02003* (2013.01); *C12Y 207/03002* (2013.01); *C12Q 1/34* (2013.01)

(58) Field of Classification Search
None
See application file for complete search history.

(56) References Cited

U.S. PATENT DOCUMENTS

| | | | |
|---|---|---|---|
| 5,916,761 A | 6/1999 | Koga et al. | |
| 7,338,775 B1 * | 3/2008 | Ostanin .................. | C12Q 1/26 435/17 |
| 2002/0119507 A1 | 8/2002 | Kishimoto et al. | |
| 2012/0040387 A1 | 2/2012 | Matsuoka | |

FOREIGN PATENT DOCUMENTS

| | | |
|---|---|---|
| EP | 0639646 A1 | 2/1995 |
| EP | 08881301 A1 | 2/1998 |
| JP | S60-047698 A | 3/1985 |
| JP | H03-180200 A | 8/1991 |
| JP | H03-224498 A | 10/1991 |
| JP | H04-335898 A | 11/1992 |
| JP | H07-155199 A | 6/1995 |
| JP | H07-177898 A | 7/1995 |
| JP | H09-285297 A | 11/1997 |
| JP | 2002-355095 A | 12/2002 |
| JP | 2006-223163 A | 8/2006 |
| JP | 2017038569 A | 2/2017 |
| WO | WO2010-082665 A | 7/2010 |
| WO | 2011056611 A | 5/2011 |

OTHER PUBLICATIONS

Tanzer et al, Journal of Biological Chemistry, 1959, vol. 234, No. 12, pp. 3201-3204. (Year: 1959).*
International Search Report issued in International Application No. PCT/JP2015/076639, dated Dec. 22, 2015.
International Preliminary Report on Patentability in International Application No. PCT/JP2015/076639, dated Mar. 28, 2017.
Takahiko Kato, Chapter 9: Enzymatic cycling, Lectures on Biochemical Experiments 5, Method for Researching Enzymes (1), ed. The Japanese Biochemical Society, Tokyo Kagaku Dojin, 1975, pp. 121-135.
Enzymes I: Guide to Biotechnology, The Japan Society for Bioscience, Biotechnology, and Agrochemistry, Asakura Publishing Co. Ltd., 1985, pp. 97-101.
Matsuoka et al.: "An ultrasensitive enzymatic method for measuring mevalonic acid in serum.", J Lipid Res., 2012, vol. 53, No. 9, pp. 1987-1992.

(Continued)

*Primary Examiner* — Allison M Fox
(74) *Attorney, Agent, or Firm* — Greenblum & Bernstein, P.L.C.

(57) ABSTRACT

The present invention provides a measuring method for at least one of a kinase forward reaction substrate, a phosphorylated product thereof, and a precursor thereof, and includes a step of conducting an enzymatic cycling reaction by bringing at least a kinase, a first nucleotide coenzyme of the kinase, and a second nucleotide coenzyme having a different nucleoside moiety from the first nucleotide coenzyme into contact with a sample; a step of detecting a signal corresponding to a change of at least one of the first nucleotide coenzyme and a conversion product thereof, and the second nucleotide coenzyme and a conversion product thereof; and (3) a step of calculating, on the basis of the detected change of the signal, an amount of the kinase forward reaction substrate and/or the phosphorylated product thereof contained in the sample.

36 Claims, 12 Drawing Sheets

(56) References Cited

OTHER PUBLICATIONS

Ito et al., The 57th Chugoku-Shikoku Regional Congress Symposium: Laboratory Testing Up to Date(1) "Development of Super High-Sensitive Measurement of Proteins", Rinsho Byori, 2012, vol. 60, No. 11, pp. 1088-1093.
Extended European Search Report issued in European Patent Application No. 15844093.3 dated Mar. 16, 2018.
G. Grossman and O'Sullivan, W. J., "Eastern kangaroo muscle creatine kinase," Australian J. Biological Sciences (1981) 34:269-282.

* cited by examiner

MEASURING METHOD AND COMPOSITION USING KINASE

TECHNICAL FIELD

The present invention relates to a novel sensitive measuring method employing an enzymatic cycling method using a kinase, and a composition used therefor.

BACKGROUND ART

An enzymatic cycling method is a method in which a concentration of a very small amount of a substance is amplified for measurement by utilizing a function of an enzyme. Conventionally, as a method for measuring a coenzyme, a sensitive measuring method for a coenzyme such as nicotinamide adenine dinucleotide (NAD) cycling using two dehydrogenases is known (see, for example, Non Patent Literature 1). Besides, a cycling method for measuring adenosine triphosphate (ATP) similarly using two kinases has been reported (see, for example, Patent Literature 1). On the other hand, examples of an enzymatic cycling method for measuring not a coenzyme but a substrate include a method for performing measurement by using two transferases and a method for performing measurement by using one enzyme.

An example of the method using two enzymes includes a method using transaminase and polyamine oxidase (see, for example, Patent Literature 2). In this method, putrescine transaminase and polyamine oxidase are used for quantitatively determining putrescine through enzymatic cycling reactions using polyamine oxidase for a reaction from putrescine to 4-aminobutanal and using putrescine transaminase for a reverse reaction, and specifically, hydrogen peroxide produced through the polyamine oxidase reaction is measured by a known coloring method. Similarly, a method for measuring a benzylamine using a benzylamine transaminase and a benzylamine oxidase and a method for measuring tyramine using a benzylamine transaminase and a tyramine oxidase have been reported (see, for example, Patent Literatures 3 and 4).

Besides, as a measuring method employing a cycling method using one enzyme, a method using a dehydrogenase is known (see, for example, Patent Literatures 5 and 6). In this method, an enzymatic cycling reaction utilizing reversible reactivity of a dehydrogenase is caused to proceed in the presence of oxidized coenzyme NAD (P) or an analog thereof, and a reduced coenzyme NAD (P) or an analog thereof, so as to sensitively quantitatively determine a substrate for the dehydrogenase, and this method is applied to quantitative determination of bile acid using 3α-hydroxysteroid dehydrogenase in the presence of thio-NAD and reduced NAD, or quantitative determination of glucose-6-phosphate using glucose-6-phosphate dehydrogenase, for example.

Conventionally, as a measuring method for a substrate as a measurement target using a kinase, for example, a method for measuring triglyceride is known (see, for example, Non Patent Literature 2). Besides, a method for measuring creatinine is known (see, for example, Patent Literature 7). In this measuring method, creatinine is converted into creatine by a function of creatinine amidohydrolase, the creatine is further converted, in the presence of ATP, into creatine phosphate and adenosine diphosphate (ADP) by creatine kinase, then the ADP is measured for measuring the creatinine.

CITATION LIST

Patent Literature

Patent Literature 1: Japanese Patent Laid-Open No. 2006-223163
Patent Literature 2: Japanese Patent Laid-Open No. 3-180200
Patent Literature 3: Japanese Patent Laid-Open No. 7-155199
Patent Literature 4: Japanese Patent Laid-Open No. 7-177898
Patent Literature 5: Japanese Patent Laid-Open No. 3-224498
Patent Literature 6: Japanese Patent Laid-Open No. 4-335898
Patent Literature 7: Japanese Patent Laid-Open No. 9-285297

Non Patent Literature

Non Patent Literature 1: Seikagaku Jikken Kouza 5 Koso Kenkyuho (jo) (Lecture on Biochemical Experiments 5 Study Method for Enzymes (1)), edited by The Japanese Biochemical Society, Tokyo Kagaku Dojin, 1975, pp. 121-135
Non Patent Literature 2: Koso-Biotechnology eno Shishin-(Enzyme-Guideline for Biotechnology-), edited by Japan Society for Bioscience, Biotechnology, and Agrochemistry, Asakura Publishing Co., Ltd., 1985, pp. 97-101

SUMMARY OF INVENTION

Technical Problem

An object of the present invention is to provide a method and a composition by which at least one of a kinase forward reaction substrate, a phosphorylated product thereof, and a precursor thereof can be highly accurately measured.

Solution to Problem

A measuring method employing an enzymatic cycling method is a technique applicable to sensitive quantitative determination by controlling an amount of an enzyme because a signal corresponding to an enzymatic reaction increases in accordance with the amount of the enzyme to be added. In particular, a method using a kinase in an enzymatic cycling method for quantitatively determining a substrate has not yet been known, and measurement targets in the enzymatic cycling method for quantitatively determining a substrate have been limited. Further, a forward reaction usually proceeds priorly to a reverse reaction in a kinase reaction, and it has been regarded that it is technically difficult to apply a kinase to an enzymatic cycling method utilizing a reverse reaction.

On the other hand, as described above, an example of a method for measuring a substrate using a kinase includes the method for measuring creatinine using creatinine kinase (see, for example, Patent Literature 7), the kinase is used merely for a unidirectional stoichiometric conversion reaction, and therefore, if the concentration of a measurement target is low, sufficient sensitivity cannot be always obtained, and hence it is necessary to deal with this problem by, for example, increasing the amount of a specimen. If the amount of a specimen is increased, however, there arises a practical problem in which the measurement is largely affected by a coexisting substance.

Under these circumstances, the present inventors have found the following: a plurality of kinases catalyze both a forward reaction and a reverse reaction of a kinase reaction, and utilize coenzymes having different nucleoside moieties in the forward reaction and the reverse reaction, and when these kinases are used in an enzymatic cycling reaction, a kinase forward reaction substrate and/or a phosphorylated product thereof, or a precursor thereof can be surprisingly sensitively measured, and thus, the present invention was accomplished.

The present invention has, for example, the following features:

[1]

A measuring method for at least one of a kinase forward reaction substrate, a phosphorylated product thereof, and a precursor thereof, comprising:

(1) a step of conducting a cycling reaction according to the following formula (1):

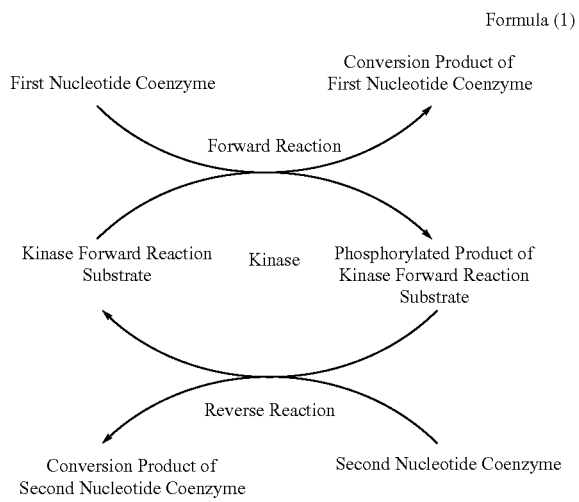

Formula (1)

by bringing a kinase catalyzing a forward reaction for producing a phosphorylated product from a kinase forward reaction substrate and a reverse reaction thereof in the presence of nucleotide coenzymes, the kinase utilizing nucleotide coenzymes at least having different nucleoside moieties in the forward reaction and the reverse reaction, respectively, a first nucleotide coenzyme of the kinase and a second nucleotide coenzyme having a different nucleoside moiety from the first nucleotide coenzyme into contact with a sample or a sample having been subjected to a quantitative derivation treatment from the precursor to the kinase forward reaction substrate and/or the phosphorylated product thereof in a case where a measurement target is the precursor;

(2) a step of detecting an amount of change of a signal corresponding to a change of at least any one of the first nucleotide coenzyme, a conversion product of the first nucleotide coenzyme, the second nucleotide coenzyme, and a conversion product of the second nucleotide coenzyme; and (3) a step of calculating, on the basis of the detected change of the signal, an amount of at least one of the kinase forward reaction substrate, the phosphorylated product thereof, and the precursor thereof contained in the sample.

[1-1]

The measuring method according to [1] described above, wherein the measurement target is the kinase forward reaction substrate and/or the phosphorylated product thereof.

[1-1-1]

The measuring method according to [1] or [1-1] described above, wherein the measurement target is the kinase forward reaction substrate and/or the phosphorylated product thereof, and a combination of the measurement target and the kinase is any one of combinations listed in the following table 1.

TABLE 1

| Target to be measured | Kinase |
| --- | --- |
| Creatine and/or phosphorylated product thereof | Creatine kinase |
| 3-Phosphoglycerate and/or phosphorylated product thereof | 3-Phosphoglycerate kinase |
| Pyruvate and/or phosphorylated product thereof | Pyruvate kinase |
| Fructose-6-phosphate and/or phosphorylated product thereof | Phosphofructo-1-kinase |
| Glycerol and/or phosphorylated product thereof | Glycerol kinase |
| Hexose and/or phosphorylated product thereof | Hexokinase |
| Glucose and/or phosphorylated product thereof | ADP-dependent glucokinase |

[1-1-2] The measuring method according to any one of [1] to [1-1-1] described above, wherein the measurement target is the kinase forward reaction substrate and/or the phosphorylated product thereof, and a combination of the measurement target and the kinase is any one of the followings. It is noted that each of the following combinations is described as a measurement target: a kinase in this order. In addition, a phosphorylated product thereof refers to a phosphorylated product corresponding to the described kinase forward reaction substrate.

Creatine/a phosphorylated product thereof: creatine kinase (EC 2.7.3.2)

3-Phosphoglycerate/a phosphorylated product thereof: 3-phosphoglycerate kinase (EC 2.7.2.3)

Pyruvate/a phosphorylated product thereof: pyruvate kinase (EC 2.7.1.40)

Fructose-6-phosphate/a phosphorylated product thereof: phosphofructo-1-kinase (EC 2.7.1.11)

Glycerol/a phosphorylated product thereof: glycerol kinase (EC 2.7.1.30)

Hexose/a phosphorylated product thereof: hexokinase (EC 2.7.1.1)

Glucose/a phosphorylated product thereof: ADP-dependent glucokinase (EC 1.7.1.147)

[1-2]

The measuring method according to [1] described above, wherein the measurement target is the precursor, and the sample is the sample having been subjected to the quantitative derivation treatment from the precursor to the kinase forward reaction substrate and/or the phosphorylated product thereof, and the amount of the precursor is calculated on the basis of the detected change of the signal.

[1-2-1]

The measuring method according to [1] or [1-2] described above, wherein the measurement target is the precursor, and a combination of the measurement target, the kinase and the kinase forward reaction substrate and/or the phosphorylated product thereof is any one of combinations listed in the following table 2.

TABLE 2

| Target to be measured | Kinase | Kinase substrate and/or phosphorylated product thereof |
|---|---|---|
| Creatinine | Creatine kinase | Creatine and/or phosphorylated product thereof |
| Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate, or 2,3-bisphosphoglycerate | 3-Phosphoglycerate kinase | 3-Phosphoglycerate and/or phosphorylated product thereof |
| Glucose-6-phosphate | Phosphofructo-1-kinase | Phosphofructose-6-phosphate and/or phosphorylated product thereof |
| Dihydroxyacetone phosphate, triglyceride, lysophosphatidylcholine, lysophosphatidate, glycerol-3-phosphate, lysophosphatidylglycerol, or phosphatidylglycerol | Glycerokinase | Glycerol and/or phosphorylated product thereof |
| Glucose-1-phosphate | ADP-dependent glucokinase | Glucose and/or phosphorylated product thereof |

[1-2-2]

The measuring method according to any one of [1], [1-2] and [1-2-1] described above, wherein the measurement target is the precursor, and a combination of the measurement target, the kinase and the kinase forward reaction substrate/the phosphorylated product thereof is any one of the followings. It is noted that each of the following combinations is described as a measurement target: a kinase: a kinase forward reaction substrate in this order.

Creatinine: creatine kinase (EC 2.7.3.2): creatine/a phosphorylated product thereof Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate or 2,3-bisphosphoglycerate: 3-phosphoglycerate kinase (EC 2.7.2.3): 3-phosphoglycerate/a phosphorylated product thereof Glucose-6-phosphate: phosphofructo-1-kinase (EC 2.7.1.11): phosphofructose-6-phosphate/a phosphorylated product thereof Hydroxyacetone phosphate, triglyceride, lysophosphatidylcholine, lysophosphatidate, glycerol-3-phosphate, lysophosphatidylglycerol, or phosphatidylglycerol: glycerokinase (EC 2.7.1.30) glycerol/a phosphorylated product thereof Glucose-1-phosphate: ADP-dependent glucokinase (EC 2.7.1.147): glucose/a phosphorylated product thereof

[1-2-3]

The measuring method according to any one of [1], [1-2] and [1-2-2] described above, wherein the measurement target is creatinine as the precursor, the kinase is creatine kinase, and the kinase forward reaction substrate is creatine.

[1-2-4]

The measuring method according to any one of [1] and [1-2] to [1-2-3] described above, wherein creatinine is brought into contact with creatinine amidohydrolase (EC 3.5.2.10) in the presence of water in the quantitative derivation treatment from the precursor to the kinase forward reaction substrate and/or the phosphorylated product thereof.

[2]

The measuring method according to any one of [1] to [1-2-4] described above, wherein the step (2) is a step of detecting an amount of change of a signal corresponding to an increased amount of the conversion product resulting from the forward reaction of the first nucleotide coenzyme or the conversion product resulting from the reverse reaction of the second nucleotide coenzyme.

[3]

The measuring method according to any one of [1] to [2] described above, wherein the nucleoside moiety of the first nucleotide coenzyme is any one of adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine, and the nucleoside moiety is different between the first nucleotide coenzyme and the second nucleotide coenzyme.

[4]

The measuring method according to any one of [1] to [3] described above, wherein the nucleoside moiety of the first nucleotide coenzyme is adenosine, inosine, guanosine or deoxyadenosine, and the nucleoside moiety is different between the first nucleotide coenzyme and the second nucleotide coenzyme.

[5]

The measuring method according to any one of [1] to [4] described above, wherein the nucleoside moiety of the second nucleotide coenzyme is any one of adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine, and the nucleoside moiety is different between the first nucleotide coenzyme and the second nucleotide coenzyme.

[6]

The measuring method according to any one of [1] to [5] described above, wherein the nucleoside moiety of the second nucleotide coenzyme is adenosine, inosine, guanosine or deoxyguanosine, and the nucleoside moiety is different between the first nucleotide coenzyme and the second nucleotide coenzyme.

[7]

The measuring method according to any one of [1] to [6] described above, wherein the nucleoside moiety of the first nucleotide coenzyme is adenosine, inosine, guanosine or deoxyadenosine, the nucleoside moiety of the second nucleotide coenzyme is adenosine, inosine, guanosine or deoxyguanosine, and the nucleoside moiety is different between the first nucleotide coenzyme and the second nucleotide coenzyme.

[7-1]

The measuring method according to any one of [1] to [7] described above, wherein a combination of the nucleoside moiety of the first nucleotide coenzyme and the nucleoside moiety of the second nucleotide coenzyme is a combination of adenosine and inosine, guanosine and adenosine, deoxyadenosine and guanosine, deoxyadenosine and deoxyguanosine, deoxyadenosine and inosine, or inosine and adenosine.

[7-2]

The measuring method according to any one of [1] to [7-1] described above, wherein the nucleoside moiety of the first nucleotide coenzyme is adenosine, and the nucleoside moiety of the second nucleotide coenzyme is inosine.

[7-3]

The measuring method according to any one of [1] to [7-3] described above, wherein the first nucleotide coenzyme is adenosine triphosphate (ATP), and the second nucleotide coenzyme is inosine diphosphate (IDP).

[8]

The measuring method according to any one of [1] to [7-3] described above, wherein in the step of detecting the amount of change of the signal, an amount of change of a signal corresponding to an increased amount of the conversion product of the first nucleotide coenzyme resulting from the forward reaction or the conversion product of the second nucleotide coenzyme resulting from the reverse reaction is detected by using a detection enzyme able to utilize the conversion product of the first nucleotide coenzyme resulting from the forward reaction but unable to utilize the second nucleotide coenzyme, or a detection enzyme unable to utilize the first nucleotide coenzyme but able to utilize the conversion product of the second nucleotide coenzyme resulting from the reverse reaction.

[9]

The measuring method according to any one of [1] to [8] described above, wherein in the step of detecting the amount of change of the signal, an amount of change of a signal varied in accordance with an increased amount of adenosine diphosphate (ADP) is detected by using adenosine diphosphate (ADP)-dependent glucokinase (EC 2.7.1.147) in the presence of glucose.

[10]

The measuring method according to any one of [1] to [9] described above, wherein in the step of detecting the amount of change of the signal, an amount of change of a signal varied in accordance with an increased amount of adenosine diphosphate (ADP) is detected by using adenosine diphosphate (ADP)-dependent glucokinase (EC 2.7.1.147) in the presence of any one of coenzymes of thionicotinamide adenine dinucleotide phosphate (thio-NADP), thionicotinamide adenine dinucleotide (thio-NAD), nicotinamide adenine dinucleotide phosphate (NADP) and nicotinamide adenine dinucleotide (NAD), glucose, and glucose 6-phosphate dehydrogenase.

[11]

The measuring method according to any one of [1] and [1-2] to [10] described above, wherein the measurement target is creatinine as the precursor, and the method comprises:

(1) a step of conducting a cycling reaction represented by the following formula (2):

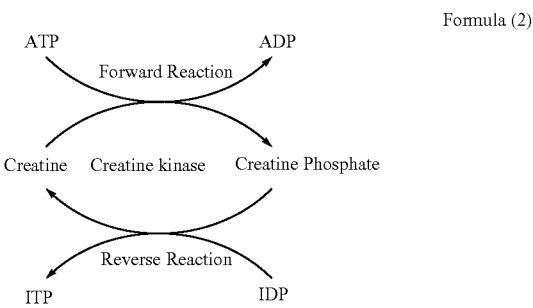

Formula (2)

by bringing the sample, the sample having been subjected to the treatment for quantitative derivation of creatine by bringing creatinine into contact with creatinine amidohydrolase (EC 3.5.2.10) in the presence of water, into contact with at least the following components (a) to (c):

(a) creatine kinase (EC 2.7.3.2),
(b) ATP, and
(c) IDP;

(2) a step of detecting, by using adenosine diphosphate-dependent glucokinase (EC 2.7.1.147), an amount of change of a signal corresponding to an increased amount of adenosine diphosphate in the presence of a coenzyme of any one of thio-NADP, thio-NAD, NADP and NAD, glucose and glucose 6-phosphate dehydrogenase; and (3) a step of calculating an amount of the creatinine contained in the sample on the basis of a detection result of the step (2).

[12]

A measuring composition for measuring at least one of a kinase forward reaction substrate, a phosphorylated product thereof, and a precursor thereof, and used after the precursor is subjected to a quantitative derivation treatment from the precursor to the kinase forward reaction substrate and/or the phosphorylated product thereof in a case where a measurement target is the precursor, comprising:

(a) a kinase that catalyzes a forward reaction for producing a phosphorylated product from the kinase forward reaction substrate and a reverse reaction thereof in the presence of nucleotide coenzymes, and utilizes nucleotide coenzymes at least having different nucleoside moieties in the forward reaction and the reverse reaction, respectively;

(b) a first nucleotide coenzyme for the forward reaction; and (c) a second nucleotide coenzyme for the reverse reaction having a different nucleoside moiety from the first nucleotide coenzyme.

[12-1]

The composition according to [12] described above, wherein the measurement target is the kinase forward reaction substrate and/or the phosphorylated product thereof.

[12-1-1]

The composition according to [12] or [12-1] described above, wherein the measurement target is the kinase forward reaction substrate and/or the phosphorylated product thereof, and a combination of the measurement target and the kinase is any one of combinations listed in the following table 3.

TABLE 3

| Target to be measured | Kinase |
| --- | --- |
| Creatine and/or phosphorylated product thereof | Creatine kinase |
| 3-Phosphoglycerate and/or phosphorylated product thereof | 3-phosphoglycerate kinase |
| Pyruvate and/or phosphorylated product thereof | Pyruvate kinase |
| Fructose-6-phosphate and/or phosphorylated product thereof | Phosphofructo-1-kinase |
| Glycerol and/or phosphorylated product thereof | Glycerol kinase |
| Hexose and/or phosphorylated product thereof | Hexokinase |
| Glucose and/or phosphorylated product thereof | ADP-dependent glucokinase |

[12-1-2]

The composition according to any one of [12] to [12-1-1] described above, wherein the measurement target is the kinase forward reaction substrate and/or the phosphorylated product thereof, and a combination of the measurement target and the kinase is any one of the followings. It is noted that each of the following combinations is described as a measurement target: a kinase in this order. In addition, a phosphorylated product thereof refers to a phosphorylated product corresponding to the described kinase forward reaction substrate.

Creatine/a phosphorylated product thereof: creatine kinase (EC 2.7.3.2)

3-Phosphoglycerate/a phosphorylated product thereof: 3-phosphoglycerate kinase (EC 2.7.2.3)

Pyruvate/a phosphorylated product thereof: pyruvate kinase (EC 2.7.1.40)

Fructose-6-phosphate/a phosphorylated product thereof: phosphofructo-1-kinase (EC 2.7.1.11)

Glycerol: glycerol kinase (EC 2.7.1.30)

Hexose/a phosphorylated product thereof: hexokinase (EC 2.7.1.1)

Glucose/a phosphorylated product thereof: ADP-dependent glucokinase (EC 2.7.1.147)

[12-2]

The composition according to [12] described above, wherein the measurement target is the precursor, and the composition is used after the precursor is subjected to the quantitative derivation treatment from the precursor to the kinase forward reaction substrate and/or the phosphorylated product thereof.

[12-2-1]

The composition according to [12] or [12-2] described above, wherein the measurement target is the precursor, and a combination of the measurement target, the kinase and the kinase forward reaction substrate and/or the phosphorylated product thereof is any one of combinations listed in the following table 4.

TABLE 4

| Target to be measured | Kinase | Kinase substrate and/or phosphorylated product thereof |
| --- | --- | --- |
| Creatinine | Creatine kinase | Creatine and/or phosphorylated product thereof |
| Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate, or 2,3-bisphosphoglycerate | 3-Phosphoglycerate kinase | 3-Phosphoglycerate and/or phosphorylated product thereof |
| Glucose-6-phosphate | Phosphofructo-1-kinase | Phosphofructose-6-phosphate and/or phosphorylated product thereof |
| Dihydroxyacetone phosphate, triglyceride, lysophosphatidylcholine, lysophosphatidate, glycerol-3-phosphate, lysophosphatidylglycerol, or phosphatidylglycerol | Glycerokinase | Glycerol and/or phosphorylated product thereof |
| Glucose-1-phosphate | ADP-dependent glucokinase | Glucose and/or phosphorylated product thereof |

[12-2-2]

The composition according to any one of [12], [12-2] and [12-2-1] described above, wherein the measurement target is the precursor, and a combination of the measurement target, the kinase and the kinase forward reaction substrate/the phosphorylated product thereof is any one of the followings. It is noted that each of the following combinations is described as a measurement target: a kinase: a kinase forward reaction substrate/a phosphorylated product thereof in this order.

Creatinine: creatine kinase (EC 2.7.3.2): creatine/a phosphorylated product thereof Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate, or 2,3-bisphosphoglycerate: 3-phosphoglycerate kinase (EC 2.7.2.3): 3-phosphoglycerate/a phosphorylated product thereof Glucose-6-phosphate: phosphofructo-1-kinase (EC 2.7.1.11): phosphofructose-6-phosphate/a phosphorylated product thereof), (dihydroxyacetone phosphate, triglyceride, lysophosphatidylcholine, lysophosphatidate, glycerol-3-phosphate, lysophosphatidylglycerol, or phosphatidylglycerol: glycerokinase (EC 2.7.1.30): glycerol/a phosphorylated product thereof Glucose-1-phosphate: ADP-dependent glucokinase (EC 2.7.1.147): glucose/a phosphorylated product thereof

[12-2-3]

The composition according to any one of [12] and [12-2] to [12-2-2] described above, wherein the measurement target is creatinine as the precursor, the kinase is creatine kinase, and the kinase forward reaction substrate is creatine.

[12-2-4]

The composition according to any one of [12] and [12-2] to [12-2-3] described above, wherein creatine is derived by bringing creatinine into contact with creatinine amidohydrolase (EC 3.5.2.10) in the presence of water in the quantitative derivation treatment from the precursor to the kinase forward reaction substrate and/or the phosphorylated product thereof.

[13]

The composition according to any one of [12] to [12-2-4] described above, wherein the nucleoside moiety of the first nucleotide coenzyme is any one of adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine, and the nucleoside moiety is different between the first nucleotide coenzyme and the second nucleotide coenzyme.

[14]

The composition according to any one of [12] to [13] described above, wherein the nucleoside moiety of the first nucleotide coenzyme is adenosine, inosine, guanosine or deoxyadenosine, and the nucleoside moiety is different between the first nucleotide coenzyme and the second nucleotide coenzyme.

[15]

The composition according to any one of [12] to [14] described above, wherein the nucleoside moiety of the second nucleotide coenzyme is any one of adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine, and the nucleoside moiety is different between the first nucleotide coenzyme and the second nucleotide coenzyme.

[16]

The composition according to any one of [12] to [15] described above, wherein the nucleoside moiety of the second nucleotide coenzyme is adenosine, inosine, guanosine or deoxyguanosine, and the nucleoside moiety is different between the first nucleotide coenzyme and the second nucleotide coenzyme.

[17]

The composition according to any one of [12] to [16] described above, wherein the nucleoside moiety of the first nucleotide coenzyme is adenosine, inosine, guanosine or deoxyadenosine, the nucleoside moiety of the second nucleotide coenzyme is inosine, guanosine, adenosine, or deoxyguanosine, and the nucleoside moiety is different between the first nucleotide coenzyme and the second nucleotide coenzyme.

[17-1]

The composition according to any one of [12] to [17] described above, wherein a combination of the nucleoside moiety of the first nucleotide coenzyme and the nucleoside moiety of the second nucleotide coenzyme is a combination of adenosine and inosine, guanosine and adenosine, deoxyadenosine and guanosine, deoxyadenosine and deoxyguanosine, deoxyadenosine and inosine, or guanosine and adenosine.

[17-2]

The composition according to any one of [12] to [17-1] described above, wherein the nucleoside moiety of the first nucleotide coenzyme is adenosine, and the nucleoside moiety of the second nucleotide coenzyme is inosine.

[17-3]

The composition according to any one of [12] to [17-2] described above, wherein the first nucleotide coenzyme is adenosine triphosphate (ATP), and the second nucleotide coenzyme is inosine diphosphate (IDP).

[18]

The composition according to any one of [12] to [17-3] described above, further comprising a detection enzyme able to utilize a conversion product of the first nucleotide coenzyme resulting from the forward reaction but unable to utilize the second nucleotide coenzyme, or a detection enzyme unable to utilize the first nucleotide coenzyme but able to utilize a conversion product of the second nucleotide coenzyme resulting from the reverse reaction.

[19]

The composition according to [18] described above, wherein the detection enzyme is adenosine diphosphate (ADP)-dependent glucokinase (EC 1.7.1.147), and the composition further comprises glucose.

[20]

The composition according to [18] described above, further comprising thionicotinamide adenine dinucleotide phosphate (thio-NADP), thionicotinamide adenine dinucleotide (thio-NAD), nicotinamide adenine dinucleotide phosphate (NADP) or nicotinamide adenine dinucleotide (NAD); and glucose-6-phosphate dehydrogenase.

[21]

The composition according to any one of [12-2] to [20] described above, wherein the measurement target is creatinine as the precursor, the composition is used after a quantitative derivation treatment from the creatinine to creatine by bringing the creatinine into contact with creatinine amidohydrolase (EC 3.5.2.10) in the presence of water, and comprises:

(a) creatine kinase;
(b) adenosine triphosphate (ATP);
(c) inosine diphosphate (IDP);
(d) adenosine diphosphate (ADP)-dependent glucokinase (EC 2.7.1.147);
(e) glucose;
(f) thionicotinamide adenine dinucleotide phosphate (thio-NADP), thionicotinamide adenine dinucleotide (thio-NAD), nicotinamide adenine dinucleotide phosphate (NADP) or nicotinamide adenine dinucleotide (NAD); and
(g) glucose-6-phosphate dehydrogenase.

[22]

A reagent kit, comprising the composition according to any one of [12] to [21] described above.

Advantageous Effects of Invention

According to the present invention, at least one of a kinase substrate, a phosphorylated product thereof, and a precursor thereof can be highly sensitively measured.

According to the present invention, a measurement target substance, which has been difficult to highly sensitively measure by a conventional cycling method, such as fructose-6-phosphate or creatinine, can be highly sensitively measured.

DESCRIPTION OF EMBODIMENT

Figure 1:
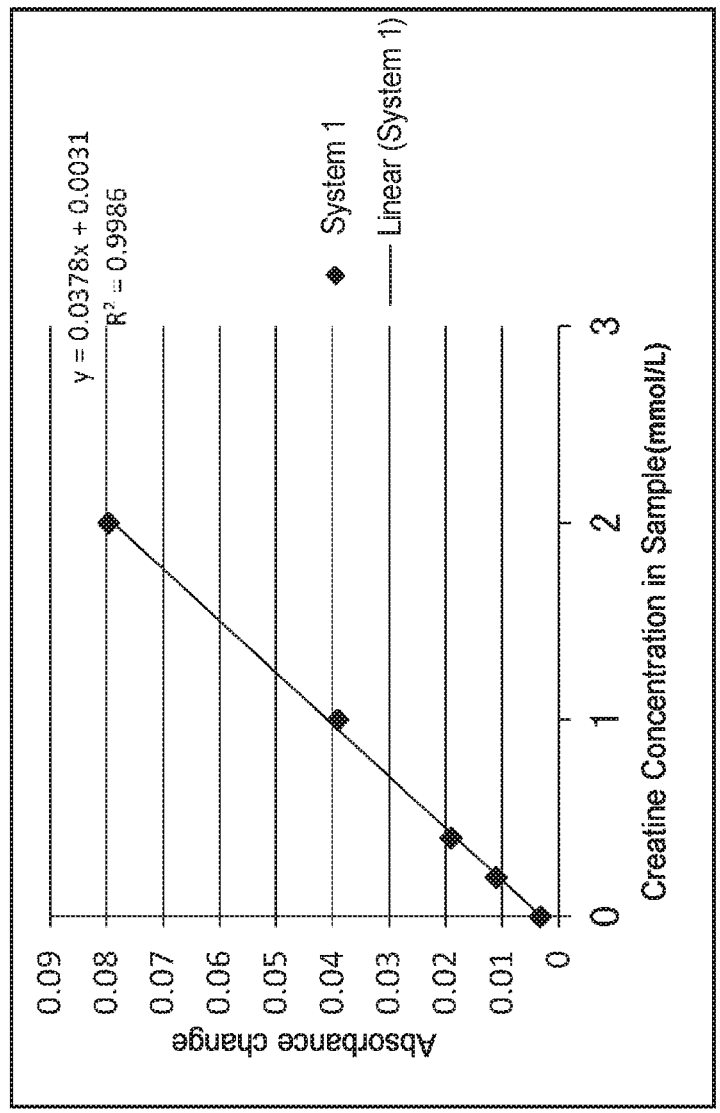
FIG. 1 is a graph illustrating the correlation between a creatine concentration in a sample and an absorbance change obtained by using a creatine kinase.

Now, an embodiment for practicing the present invention (hereinafter also referred to as the "present embodiment") will be specifically described. It should not be understood that the present invention is limited to the following embodiment. Various alternative embodiments, examples and operation techniques will be apparent, on the basis of the present disclosure, for those skilled in the art. It should be understood that the present invention embraces various embodiments and the like not described herein. It is noted that EC numbers (Enzyme Commission numbers) mentioned herein are those confirmed as of Sep. 12, 2014.

A method of the present embodiment is a measuring method for at least one of a kinase forward reaction substrate, a phosphorylated product thereof, and a precursor thereof, including:

(1) a step of conducting an enzymatic cycling reaction represented by the following formula (3):

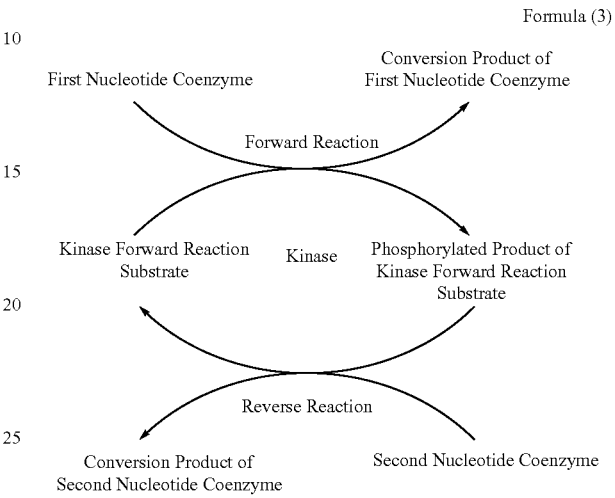

Formula (3)

by bringing a kinase catalyzing a forward reaction for producing the phosphorylated product from the kinase forward reaction substrate and a reverse reaction thereof in the presence of nucleotide coenzyme, the kinase utilizing nucleotide coenzymes at least having different nucleoside moieties in the forward reaction and the reverse reaction, respectively, a first nucleotide coenzyme of the kinase and a second nucleotide coenzyme having a different nucleoside moiety from the first nucleotide coenzyme into contact with a sample or a sample having been subjected to a quantitative derivation treatment from the precursor to the kinase forward reaction substrate and/or the phosphorylated product thereof in a case where a measurement target is a precursor;

(2) a step of detecting an amount of change of a signal corresponding to a change of at least any one of the first nucleotide coenzyme, a conversion product of the first nucleotide coenzyme, the second nucleotide coenzyme, and a conversion product of the second nucleotide coenzyme; and (3) a step of calculating, on the basis of the detected change of the signal, an amount of at least one of the kinase forward reaction substrate, the phosphorylated product thereof, and the precursor thereof contained in the sample.

The kinase used in the method of the present embodiment is, as shown in the formula (3), a kinase capable of catalyzing, in the presence of the first nucleotide coenzyme, the forward reaction for producing the phosphorylated product thereof from the forward reaction substrate, and catalyzing, in the presence of the second nucleotide coenzyme, the reverse reaction for producing the forward reaction substrate from the phosphorylated product of the forward reaction substrate.

If the measurement target is the precursor, the sample having been subjected to the quantitative derivation treatment from the precursor to the kinase forward reaction substrate and/or the phosphorylated product thereof is used as the sample.

The kinase forward reaction substrate and the phosphorylated product thereof corresponding to the measurement target in the method of the present embodiment are not especially limited as long as they can be measured by the method of the present embodiment, and examples include creatine, 3-phosphoglycerate, pyruvate, fructose-6-phosphate, glycerol, and phosphorylated products of these. Besides, examples of the precursor thereof include, but are not limited to, creatinine, glyceraldehyde-3-phosphate, dihydroxyacetone phosphate, glycerol-3-phosphate, lysophosphatidate, lysophosphatidylcholine, fructose-1,6-bisphosphate, 2-phosphoglycerate, phosphoenolpyruvate, 2,3-bisphosphoglycerate, glucose-6-phosphate, triglyceride, phosphatidylcholine, phosphatidylglycerol, lysophosphatidylglycerol, and glucose-1-phosphate. For example, the precursor is preferably creatinine.

In the method of the present embodiment, the sample to be tested for the amount, contained therein, of the kinase forward reaction substrate and/or the phosphorylated product thereof, or the precursor thereof is not especially limited, and is, for example, a biological sample of a human or an animal, preferably human blood, and further preferably human serum. It should be noted that it may be unknown before performing the method whether or not the sample contains the measurement target, such as the kinase forward reaction substrate and/or the phosphorylated product thereof, or the precursor thereof. The method of the present embodiment can be performed to reveal that the sample does not contain the kinase forward reaction substrate and/or the phosphorylated product thereof, or the precursor thereof.

In the method of the present embodiment, the "precursor" refers to a substance from which to the kinase forward reaction substrate and/or the phosphorylated product thereof is derived. If there are a plurality of reaction steps to obtain the kinase forward reaction substrate and/or the phosphorylated product thereof, the precursor embraces a starting material thereof and all intermediates, and can be any of these.

In the method of the present embodiment, the "quantitative derivation treatment" refers to a treatment for deriving, from the precursor, the kinase forward reaction substrate and/or the phosphorylated product thereof in such a manner that a decreased amount of the precursor corresponds to an increased amount of the kinase forward reaction substrate and/or the phosphorylated product thereof those are derived products. Specifically, it can be any treatment by which the amount of the precursor can be calculated by the method of the present embodiment on the basis of an amount of change of a signal corresponding to a change of at least any one of the first nucleotide coenzyme, the conversion product of the first nucleotide coenzyme, the second nucleotide coenzyme, and the conversion product of the second nucleotide coenzyme. Examples of the quantitative derivation treatment include, but are not limited to, known chemical treatments. Examples of the chemical treatments include, but are not limited to, treatment using chemical reactions such as hydrolysis, oxidation and reduction. A specific example includes hydrolysis using an acid or an alkali.

Examples of the treatment, excluding the chemical treatments, include enzymatic treatments. For example, from creatinine, creatine can be derived by bringing it into contact with creatinine amidohydrolase (creatininase) (EC 3.5.2.10) in the presence of water. Accordingly, in the method of the present embodiment, if creatine is measured by using creatine kinase as the kinase, creatinine, that is, a precursor of creatine, can be measured.

In addition, since, from triglyceride, glycerol can be derived by lipase (EC 3.1.1.3), triglyceride can be measured when combined with an enzymatic cycling reaction of glycerokinase.

Furthermore, choline and glycerol-3-phosphate are derived from lysolecithin by lysophospholipase (EC 3.1.1.5) and glycerophosphocholine phosphodiesterase (EC 3.1.4.2). Accordingly, if glycerol-3-phosphate is measured by conducting an enzymatic cycling reaction of glycerokinase with derived glycerol-3-phosphate used as a substrate, lysolecithin can be also measured. It is noted that the enzymatic treatments are not limited to these.

The kinase usable in the method of the present embodiment is not especially limited as long as it is capable of catalyzing, in the presence of nucleotide coenzymes, the forward reaction for producing a phosphorylated product from a kinase forward reaction substrate, and the reverse reaction thereof, and has a characteristic that nucleotide coenzymes at least having different nucleoside moieties can be used in the forward reaction and the reverse reaction, respectively. Here, the "kinase forward reaction" performed in the method of the present embodiment refers to a reaction in a direction to transfer phosphoric acid from a nucleotide coenzyme to a forward reaction substrate among high-energy phosphotransfers catalyzed by a kinase, and the number of phosphoric acids to be transferred is not limited. Preferably, the number of phosphoric acids to be transferred is one. Besides, the "kinase reverse reaction" refers to a reaction in a reverse direction to the "kinase forward reaction".

In the present embodiment, if the measurement target is the kinase forward reaction substrate and/or the phosphorylated product thereof, examples of a combination of the measurement target and the kinase include, but are not limited to, the followings. It is noted that each of the following combinations is described as a measurement target: a kinase in this order. In addition, a phosphorylated product thereof refers to a phosphorylated product corresponding to the described kinase forward reaction substrate.

Creatine and/or a phosphorylated product thereof: creatine kinase

3-Phosphoglycerate and/or a phosphorylated product thereof: 3-phosphoglycerate kinase Pyruvate and/or a phosphorylated product thereof: pyruvate kinase Fructose-6-phosphate and/or a phosphorylated product thereof: phosphofructo-1-kinase Glycerol and/or a phosphorylated product thereof: glycerol kinase Hexose and/or a phosphorylated product thereof: hexokinase Glucose and/or a phosphorylated product thereof: adenosine diphosphate (ADP)-dependent glucokinase Preferable examples include, but are not limited to, the following combinations each including a kinase specified by EC number (Enzyme Commission number).

Creatine and/or a phosphorylated product thereof: creatine kinase (EC 2.7.3.2)

3-Phosphoglycerate and/or a phosphorylated product thereof: 3-phosphoglycerate kinase (EC 2.7.2.3)

Pyruvate and/or a phosphorylated product thereof: pyruvate kinase (EC 2.7.1.40)

Fructose-6-phosphate and/or a phosphorylated product thereof: phosphofructo-1-kinase (EC 2.7.1.11)

Glycerol and/or a phosphorylated product thereof: glycerol kinase (EC 2.7.1.30)

Hexose and/or a phosphorylated product thereof: hexokinase (EC 2.7.1.1)

Glucose and/or a phosphorylated product thereof: ADP-dependent glucokinase (EC 2.7.1.147)

If the measurement target is the precursor, examples of each combination of the measurement target, the kinase and the kinase forward reaction substrate and/or the phosphorylated product thereof include, but are not limited to, the followings. It is noted that each of the following combinations is described as a measurement target: a kinase: a kinase forward reaction substrate and/or the phosphorylated product thereof in this order.

Creatinine: creatine kinase: creatine and/or a phosphorylated product thereof

Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate, or 2,3-bisphosphoglycerate: 3-phosphoglycerate kinase: 3-phosphoglycerate and/or a phosphorylated product thereof Glucose-6-phosphate: phosphofructo-1-kinase: phosphofructose-6-phosphate and/or a phosphorylated product thereof Dihydroxyacetone phosphate, triglyceride, lysophosphatidylcholine, lysophosphatidate, glycerol-3-phosphate, lysophosphatidylglycerol, or phosphatidylglycerol: glycerokinase: glycerol and/or a phosphorylated product thereof Glucose-1-phosphate: ADP-dependent glucokinase: glucose and/or a phosphorylated product thereof Preferable examples include, but are not limited to, the following combinations each including a kinase specified by EC number:

Creatinine: creatine kinase (EC 2.7.3.2): creatine and/or a phosphorylated product thereof Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate, or 2,3-bisphosphoglycerate: 3-phosphoglycerate kinase (EC 2.7.2.3): 3-phosphoglycerate and/or a phosphorylated product thereof Glucose-6-phosphate: phosphofructo-1-kinase (EC 2.7.1.11): phosphofructose-6-phosphate and/or a phosphorylated product thereof Hydroxyacetone phosphate, triglyceride, lysophosphatidylcholine, lysophosphatidate, glycerol-3-phosphate, lysophosphatidylglycerol, or phosphatidylglycerol: glycerokinase (EC 2.7.1.30): glycerol and/or a phosphorylated product thereof Glucose-1-phosphate: ADP-dependent glucokinase (EC 2.7.1.147): glucose and/or a phosphorylated product thereof A preferable example of the combination of the measurement target, the kinase, and the kinase forward reaction substrate and/or the phosphorylated product thereof includes the following:

Creatinine: creatine kinase: creatine and/or a phosphorylated product thereof

If the measurement target is the kinase forward reaction substrate and/or the phosphorylated product thereof, each combination of the measurement target and the kinase employed in the method of the present embodiment can be determined by the following method in addition to the examples mentioned above. In addition, if the measurement target is the precursor, each combination of the measurement target, the kinase and the kinase forward reaction substrate and/or the phosphorylated product thereof can be determined by the following method in addition to the examples mentioned above.

If the measurement target is the kinase forward reaction substrate and/or the phosphorylated product thereof, a specific kinase is first selected with reference to, for example, an enzyme handbook (Asakura Publishing Co., Ltd., 1982) or the like. If information on whether or not a reverse reaction proceeds, or literature information on specificity to a nucleotide coenzyme is available, these information is referred to for the selection. Besides, if no literature information is available, these information can be actually confirmed by performing a known method such as high-performance liquid chromatography (HPLC) in combination. For example, if literature information on a reverse reaction is not available, it can be detected whether or not a reverse reaction proceeds as follows: With respect to a specific kinase, a reaction is caused by an ordinary method with the kinase added under conditions where a reverse reaction substrate and a nucleotide coenzyme are excessively present, and a product (a forward reaction substrate) or a conversion product of the nucleotide coenzyme is detected by an existing method.

For example, if a reverse reaction of glycerol kinase is to be investigated, although this method is not restrictive, a kinase reaction is caused to proceed by adding glycerol-3-phosphate corresponding to the reverse reaction substrate and ADP in excessive amounts, and the thus produced glycerol or adenosine triphosphate (ATP) is detected by an existing method. Specifically, if glycerol is to be detected, it can be detected as hydrogen peroxide by using a glycerol oxidase. Alternatively, if ATP is to be detected, the HPLC or an existing enzymatic method for detecting ATP is employed in combination. When the reverse reaction is found to proceed, if optimal pH for the reverse reaction is investigated by changing the pH at the time of the reaction, it can be used as a reference in setting conditions for practicing the method of the present embodiment. Similarly, the specificity of a nucleotide coenzyme of the forward reaction and/or the reverse reaction can be also confirmed by employing the HPLC in combination. It is to be desired that the kinase used in the method of the present embodiment has specificity of 4% or more, preferably 8% or more to nucleotide coenzymes having different nucleoside moieties respectively working the best in the forward reaction and the reverse reaction, but this is not restrictive.

Next, the forward reaction substrate or the phosphorylated product thereof to be used in combination with the kinase is selected. The selection of the forward reaction substrate or the phosphorylated product thereof may be made depending on the Michaelis constant Km of the kinase to the forward reaction substrate or the phosphorylated product thereof in some cases. For example, the Michaelis constant Km is preferably as small as possible. Specifically, it is further preferable that the Km value is 100 mmol/L, and preferably 50 mmol/L or less, but this is not restrictive.

If the forward reaction substrate and/or the phosphorylated product thereof of the kinase is a hydrolysate or an oxidant of a given substance, such a precursor can be the measurement target. Specifically, such a precursor can be converted through a known chemical treatment into the kinase forward reaction substrate and/or the phosphorylated product thereof. Further, a metabolic pathway for the conversion to the kinase forward reaction substrate and/or the phosphorylated product thereof is confirmed based on a metabolic map or the like, and if enzymes pertaining to the reaction are easily available, the precursor can be the measurement target.

The "nucleotide coenzyme" used in the method of the present embodiment refers to a phosphorylated product of nucleoside working as a coenzyme of a kinase. The first nucleotide coenzyme and the second nucleotide coenzyme used in the method of the present embodiment are nucleotide coenzymes having different nucleoside moieties from each other. The type of the nucleoside moiety of the nucleotide coenzyme used in the method of the present embodiment is not especially limited, and examples include adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine. Besides, phosphorylated products of these may be a monophosphorylated product, a diphosphorylated product or a triphosphorylated product.

Examples of the nucleotide coenzyme include ribonucleotide and deoxyribonucleotide.

Specific examples of the ribonucleotide used as the nucleotide coenzyme include, but are not limited to, ATP, ADP, adenylate (AMP), guanosine triphosphate (GTP), guanosine diphosphate (GDP), guanylate (GMP), 5-methyluridine triphosphate (TTP), 5-methyluridine diphosphate (TDP), 5-methyluridine monophosphate (TMP), uridine triphosphate (UTP), uridine diphosphate (UDP), uridine monophosphate (UMP), cytidine triphosphate (CTP), cytidine diphosphate (CDP), cytidine monophosphate (CMP), xanthosine triphosphate (XTP), xanthosine diphosphate (XDP), xanthosine monophosphate (XMP), inosine triphosphate (ITP), inosine diphosphate (IDP) and inosine monophosphate (IMP).

Besides, specific examples of the deoxyribonucleotide used as the nucleotide coenzyme include, but are not limited to, deoxyadenosine triphosphate (dATP), deoxyadenosine diphosphate (dADP), deoxyadenosine monophosphate (dAMP), deoxyguanosine triphosphate (dGTP), deoxyguanosine diphosphate (dGDP), deoxyguanosine monophosphate (dGMP), thymidine triphosphate (dTTP), thymidine diphosphate (dTDP), thymidine monophosphate (dTMP), deoxyuridine triphosphate (dUTP), deoxyuridine diphosphate (dUDP), deoxyuridine monophosphate (dUMP), deoxycytidine triphosphate (dCTP), deoxycytidine diphosphate (dCDP), deoxycytidine monophosphate (dCMP), deoxyxanthosine triphosphate (dXTP), deoxyxanthosine diphosphate (dXDP), deoxyxanthosine monophosphate (dXMP), deoxyinosine triphosphate (dITP), deoxyinosine diphosphate (dIDP) and deoxyinosine monophosphate (dIMP).

Preferable examples of the nucleotide coenzyme include, but are not limited to, ATP, ADP, GTP, GDP, TTP, TDP, UTP, UDP, CTP, CDP, XTP, XDP, ITP, IDP, dATP, dADP, dGTP, dGDP, dTTP, dTDP, dUTP, dUDP, dCTP, dCDP, dXTP, dXDP, dITP and dIDP.

To such a nucleotide enzyme, for example, substituent having coloring ability or the like may be bonded in some cases.

The nucleoside moiety of the first nucleotide coenzyme used in the forward reaction in the method of the present embodiment is not especially limited, and examples include adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine. Preferable examples include adenosine, inosine, guanosine and deoxyadenosine. A more preferable example includes adenosine. Besides, the phosphorylated products of these may be a monophosphorylated product, a diphosphorylated product or a triphosphorylated product, and a triphosphorylated product is preferred. Specific examples of the first nucleotide coenzyme include the aforementioned specific examples, and further preferable examples include ATP, GTP, TTP, UTP, CTP, XTP, ITP, dATP, dGTP, dTTP, dUTP, dCTP, dXTP and dITP.

The nucleoside moiety of the second nucleotide coenzyme used in the reverse reaction in the method of the present embodiment is not especially limited, and examples include adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine. Preferable examples include inosine, guanosine, adenosine and deoxyguanosine. A more preferable example includes inosine. Besides, the phosphorylated products of these may be a monophosphorylated product, a diphosphorylated product or a triphosphorylated product, and a diphosphorylated product is preferred. Specific examples of the second nucleotide coenzyme include the aforementioned specific examples, and further preferable examples include ADP, GDP, TDP, UDP, CDP, XDP, IDP, dADP, dGDP, dTDP, dUDP, dCDP, dXDP and dIDP.

Preferable nucleoside moieties of the first nucleotide coenzyme and the second nucleotide coenzyme used in the method of the present embodiment are not especially limited, and examples include adenosine, inosine, guanosine or deoxyadenosine, and the nucleoside moieties are different from each other. Examples of the combination of the nucleoside moiety of the first nucleotide coenzyme and the nucleoside moiety of the second nucleotide coenzyme include combinations of adenosine and inosine, guanosine and adenosine, deoxyadenosine and guanosine, deoxyadenosine and deoxyguanosine, deoxyadenosine and inosine, or inosine and adenosine. More preferably, the nucleoside moiety of the first nucleotide coenzyme is adenosine, and the nucleoside moiety of the second nucleotide coenzyme is inosine.

In the method of the present embodiment, the "conversion product of the first nucleotide coenzyme resulting from the forward reaction" refers to a dephosphorylated product of the first nucleotide coenzyme obtained in the kinase forward reaction after phosphoric acid is transferred from the first nucleotide coenzyme to the kinase forward reaction substrate. Besides, the "conversion product of the second nucleotide coenzyme resulting from the reverse reaction" refers to a phosphorylated product of the second nucleotide coenzyme obtained in the kinase reverse reaction after phosphoric acid is transferred from the kinase reverse reaction substrate to the second nucleotide coenzyme. Here, the number of phosphoric acids to be transferred may be one, two, or three. The number is preferably one.

In the step (1) of the method of the present embodiment, the cycling reaction of the formula (3) is caused, for example, as follows:

For example, the first and second nucleotide coenzymes are prepared in an excessive amount, specifically, 0.1 mmol/L or more and 12 mmol/L or less, more preferably 0.2 mmol/L to 6 mmol/L, and to the resultant, a pH buffer solution for retaining pH during a reaction is added in a concentration of 20 mmol/L or more and 200 mmol/L or less to obtain a reaction solution. The pH during the reaction may be appropriately selected as a condition for conducting the reaction to efficiently proceed, and is usually adjusted to around neutral of pH 5.5 or more and pH 8.5 or less, and a metal salt such as magnesium chloride, that is, a kinase activating agent, is added in a concentration of 0.5 mmol/L or more and 10 mmol/L or less. To the resultant, the aforementioned kinase is added, the reaction solution is precedently heated to 25° C. or more and 42° C. or less, more preferably to the vicinity of 37° C., and the forward reaction substrate and/or the phosphorylated product thereof in a smaller amount as compared with the concentration of the first and second nucleotide coenzymes was added to start the reaction.

The amount of the enzyme to be added will now be described. In a general enzymatic cycling reaction, the cycling rate depends on the amount of an enzyme, and it is known that as the Michaelis constant (the Km value) to a substrate is smaller, higher sensitivity can be attained with a smaller amount of the enzyme. Therefore, as a rough standard of the amount of the enzyme to be added, an amount corresponding to an enzyme unit (unit: u) equal to or more of, and preferably twice, as much as or more of, a larger Km value (mmol/L) between those of the forward reaction substrate and the phosphorylated product thereof is added per 1 mL of the reaction solution, and as for the upper limit, an amount that can be substantially added may be added. A Km value can be obtained also by a known method. It is noted that the amounts mentioned herein are given merely as examples and are not restrictive.

Hereinafter, the description will be made on the assumption of a creatine kinase (CK) as a specific example of the kinase, but the kinase is not limited to this. The CK is an enzyme widely present in the animal kingdom, and is abundantly contained in skeletal muscles, heart muscles, brains and the like. CKs derived from rabbits, cows, pigs, chickens and the like are commercially available, and information on the specificity of nucleotide coenzymes can be obtained from literatures. With respect to, for example, a rabbit muscle CK, it has been reported that IDP shows relative activity of 29% assuming that the activity of ADP is 100% (J Biol Chem., 241, 3116-3125, 1966). Besides, when hydrogen peroxide is produced, by using creatine amidohydrolase (EC 3.5.3.3.) and sarcosine oxidase (EC 1.5.3.1), from creatine, which is produced, for example, by using nucleoside diphosphate excluding ADP through a reverse reaction using creatine phosphate as a substrate, and the thus produced hydrogen peroxide is quantitatively determined, the specificity of the CK to the nucleoside diphosphate excluding ADP can be easily confirmed. For example, the CK derived from rabbit muscle has high specificity to IDP, and hence, ATP can be selected as the first nucleotide coenzyme used in the forward reaction, and IDP can be selected as the second nucleotide used in the reverse reaction.

In order to perform the cycling reaction of the method of the present embodiment, the pH dependency may be examined in the presence of the two nucleotide coenzymes, so as to appropriately select pH suitable for efficient proceeding of the cycling reaction. For example, with respect to a CK derived from rabbit muscle or human muscle, a buffer solution around neutral of pH 6 or more and pH 8 or less may be optimally used in some cases. Then, in the presence of excessive amounts, more specifically, 0.1 mmol/L or more and 12 mmol/L or less, preferably 0.2 mmol/L or more and 6 mmol/L or less, of ADP and IDP, creatine or creatine phosphate in a smaller amount than the ADP and the IDP, and enzyme CK may be added. With respect to the additive amount of the enzyme, it has been reported that the Km value of, for example, the CK derived from rabbit muscle to creatine and creatine phosphate are respectively 16 mmol/L and 5 mmol/L (J Biol Chem. 210, p. 65, 1954). In accordance with the above-described rough standard of the additive amount of the enzyme, these values respectively correspond to 16 u/mL and 32 u/mL. Accordingly, the enzyme may be added in a concentration of preferably 32 u/mL or more with an upper limit of about 800 u/mL, but these are not restrictive.

In the step (2) of the method of the present embodiment, an amount of change of a signal corresponding to a change of any one of the first nucleotide coenzyme, the conversion product of the first nucleotide coenzyme resulting from the forward reaction, the second nucleotide coenzyme, and the conversion product of the second nucleotide coenzyme resulting from the reverse reaction may be detected. Besides, the change of the signal may be a decreased amount of the first nucleotide coenzyme or the second nucleotide coenzyme, or an increased amount of the conversion product of the first nucleotide coenzyme resulting from the forward reaction or the conversion product of the second nucleotide coenzyme resulting from the reverse reaction. Preferably, it is the increased amount of the conversion product of the first nucleotide coenzyme resulting from the forward reaction or the conversion product of the second nucleotide coenzyme resulting from the reverse reaction. As a method for detecting the change, any of known methods such as the HPLC can be employed. If the HPLC is employed, after terminating the enzymatic reaction by adding a chelating agent or the like, the conversion product of the first nucleotide resulting from the forward reaction or the conversion product of the second nucleotide coenzyme resulting from the reverse reaction may be appropriately selected to be quantitatively determined by using a reverse phase column or the like. Such information on the HPLC analysis is easily available from resin manufacturers.

Besides, in the step (2) of the method of the present embodiment, a detection enzyme able to utilize the conversion product of the first nucleotide coenzyme resulting from the forward reaction but unable to utilize the second nucleotide coenzyme may be used for detecting an amount of change of a signal varied in accordance with the increased amount of the conversion product of the first nucleotide coenzyme resulting from the forward reaction. Alternatively, a detection enzyme unable to utilize the first nucleotide coenzyme but able to utilize the conversion product of the second nucleotide coenzyme resulting from the reverse reaction may be used for detecting an amount of change of a signal varied in accordance with the increased amount of the conversion product of the second nucleotide coenzyme resulting from the reverse reaction.

For example, a method in which an amount of change of a signal corresponding to the increased amount of ADP is detected in the presence of glucose by using adenosine diphosphate-dependent glucokinase (ADP-dependent glucokinase, EC 2.7.1.147) may be employed. It is known that ADP-dependent glucokinase derived from *Pyrococcus furiosus* can utilize, as the nucleotide coenzyme, CDP in addition to ADP, but works merely slightly on GDP and IDP. Accordingly, if the ADP-dependent glucokinase is caused to coexist as a detection enzyme in the kinase cycling reaction using ATP as the first nucleotide coenzyme and the IDP or GDP as the second nucleotide coenzyme, ADP, that is, the conversion product of the first nucleotide coenzyme resulting from the forward reaction, alone can be specifically detected. This is actually confirmed as described later.

Besides, it has been reported that glycerol kinase derived from *E. coli* uses ATP alone as a phosphate donor. Accordingly, in a case where for example, a kinase using ITP, GTP or CTP as the first nucleotide coenzyme, and using ADP as the second nucleotide coenzyme is used in the method of the present embodiment, if glycerol kinase derived from *E. coli* is used as a detection enzyme, ATP alone can be specifically detected. As the detection enzyme for specifically detecting ATP alone, other kinases specific to ATP alone can be used in addition to the glycerol kinase derived from *E. coli*, and the specificity of nucleotide coenzymes may be appropriately selected with reference to literature information. Besides, a large number of enzymes out of synthetic enzymes belonging to the enzyme commission number E 6 have been reported to specifically detect ATP alone, and hence, such enzymes can be used as the detection enzyme in a detection reaction. For example, it has been reported that NAD synthetase derived from E. coli (EC 6.3.1.5) does not work on nucleotide coenzymes excluding ATP. In this manner, in the step (2) of the method of the present embodiment, the detection enzyme to be usable may be appropriately selected in consideration of the combination of the first nucleotide coenzyme and the second nucleotide coenzyme of the kinase used in the method of the present embodiment. There is, however, a possibility that the specificity to a coenzyme depends not only on the origin of the enzyme but also on other conditions such as the additive amounts of the coenzymes and the enzyme. Therefore, a result different from that reported in a literature may be obtained in some cases, and hence, the specificity may be actually confirmed for the selection.

Preferably, the adenosine diphosphate-dependent glucokinase (EC 2.7.1.147) is used as the detection enzyme. If the ADP-dependent glucokinase is used, a product, that is, AMP or glucose-6-phosphate, can be quantitatively determined by a known method. In some cases, the glucose-6-phosphate can be used for detecting an amount of change of a signal varied in accordance with the increased amount of ADP in the presence of a coenzyme of any one of thio-NADP, thio-NAD, NADP and NAD, glucose and glucose-6-phosphate dehydrogenase. For example, the glucose-6-phosphate can be measured, in the presence of NAD (P) using glucose-6-phosphate dehydrogenase (G6PDH), as an absorbance change at 340 nm based on reduced NAD (P). Alternatively, instead of NAD (P), a coenzyme analog such as thio-NAD (P) can be used.

In the measurement of the reduced NAD (P), quantitative determination can be made also by using an electron carrier of 1-methoxy PMS in the presence of a hydrogen acceptor, such as nitrotetrazolium blue (Nitro-NB), 2-(4-iodophenyl)-3-(4-nitrophenyl)-5-(2,4-disulfophenyl)-2H-tetrazolium, sodium salt (WST-1), and 2-(4-iodophenyl)-3-(2,4-dinitrophenyl)-5-disulfophenyl)-2H-tetrazolium, sodium salt (WST-3), or by measuring an absorbance of a visible portion as a formazan dye using the enzyme diaphorase. Such compounds can be easily purchased. Besides, it can be detected by using a fluorescent reagent or a luminescent reagent in combination. Alternatively, glucose-6-phosphate can be highly sensitively quantitatively determined by an enzymatic cycling method using G6PDH (see, for example, Patent Literature 7). The step of detecting changes of these varying signals can be performed simultaneously with or separately from the cycling reaction performed in the method of the present embodiment. Similarly, also when glycerol kinase derived from E. coli is used, a product, that is, glycerol-3-phosphate, can be quantitatively determined by a known method.

It should be noted that, although the method of the present embodiment can be performed by using one kinase, the cycling reaction can be carried out using two or more enzymes different in origin but catalyzing the same reaction.

In the method of the present embodiment, as a method for calculating the amount of the kinase forward reaction substrate and/or the phosphorylated product thereof, or the precursor thereof contained in the sample, any of known methods can be employed. For example, in the enzymatic cycling reaction, the conversion product of the first nucleotide coenzyme resulting from the forward reaction and the conversion product of the second nucleotide coenzyme resulting from the reverse reaction tend to increase in proportion to the time. In order to calculate the amount of a test substance in a sample, a reaction time of the enzymatic cycling reaction is specified (to, for example, minute 5 to minute 7 after starting the reaction), and with a substance having a known concentration used as a reference (a calibrator) set as a control, an amount of change of a signal corresponding to a conversion product of the calibrator is measured, and thus, the amount of the test substance in the sample can be calculated. As the calibrator, the kinase forward reaction substrate or the phosphorylated product thereof can be used.

If there is one or a plurality of steps of introducing the precursor to the kinase forward reaction substrate and/or the phosphorylated product of the forward reaction substrate, the enzymatic cycling reaction may be performed after performing the step of introducing the precursor to the kinase forward reaction substrate and/or the phosphorylated product of the forward reaction substrate. Besides, in a case where the step of introducing the precursor to the kinase forward reaction substrate and/or the phosphorylated product of the forward reaction substrate is an enzymatic reaction, it can be introduced to the kinase forward reaction substrate and/or the phosphorylated product of the forward reaction substrate in a short time by adding an excessive amount of an enzyme catalyzing the derivation reaction, and therefore, the cycling reaction of the method of the present embodiment can be performed with the kinase precedently contained. In this case, a prescribed time after completing the derivation reaction may be specified as the reaction time.

In a case where the forward reaction substrate and the phosphorylated product thereof are mixedly contained in the sample, if merely one of the forward reaction substrate and the phosphorylated product is desired to be quantitatively determined, for example, a treatment for converting the substance not to be measured into a different substance may be performed by a known method before the enzymatic cycling reaction.

Further, the present embodiment provides a measuring composition for at least one of a kinase forward reaction substrate, a phosphorylated product thereof, and a precursor thereof, the composition comprising: (a) a kinase, which catalyzes a forward reaction for producing a phosphorylated product from the kinase forward reaction substrate and a reverse reaction thereof in the presence of nucleotide coenzymes, and utilizes nucleotide coenzymes at least having different nucleoside moieties respectively in the forward reaction and the reverse reaction; (b) a first nucleotide coenzyme used in the forward reaction; and (c) a second nucleotide coenzyme having a different nucleoside moiety from the first nucleotide coenzyme, and used in the reverse reaction, and in a case where a measurement target is the precursor, the composition is used after the precursor is subjected to a quantitative derivation treatment from the precursor to the kinase forward reaction substrate and/or the phosphorylated product thereof.

As mentioned above, the kinase of the composition according to the present embodiment is not especially limited as long as it is capable of catalyzing, in the presence of nucleotide coenzymes, the forward reaction for producing, from the kinase forward reaction substrate, the phosphorylated product thereof, and the reverse reaction thereof, and has a characteristic that nucleotide coenzymes at least having different nucleoside moieties can be respectively used in the forward reaction and the reverse reaction.

In a case where the measurement target by the composition according to the present embodiment is the kinase forward reaction substrate and/or the phosphorylated product thereof, examples of each combination of the measurement target and the kinase include, but are not limited to, the followings. It is noted that each of the following combinations is described as a measurement target: a kinase in this order. In addition, a phosphorylated product thereof refers to a phosphorylated product corresponding to the described kinase forward reaction substrate.

Creatine and/or a phosphorylated product thereof: creatine kinase

3-Phosphoglycerate and/or a phosphorylated product thereof: 3-phosphoglycerate kinase Pyruvate and/or a phosphorylated product thereof: pyruvate kinase Fructose-6-phosphate and/or a phosphorylated product thereof: phosphofructo-1-kinase Glycerol and/or a phosphorylated product thereof: glycerol kinase Hexose and/or a phosphorylated product thereof: hexokinase Glucose and/or a phosphorylated product thereof: ADP-dependent glucokinase Preferable examples include, but are not limited to, the following combinations each including a kinase specified by EC number.

Creatine and/or a phosphorylated product thereof: creatine kinase (EC 2.7.3.2)

3-Phosphoglycerate and/or a phosphorylated product thereof: 3-phosphoglycerate kinase (EC 2.7.2.3)

Pyruvate and/or a phosphorylated product thereof: pyruvate kinase (EC 2.7.1.40)

Fructose-6-phosphate and/or a phosphorylated product thereof: phosphofructo-1-kinase (EC 2.7.1.11)

Glycerol and/or a phosphorylated product thereof: glycerol kinase (EC 2.7.1.30)

Hexose and/or a phosphorylated product thereof: hexokinase (EC 2.7.1.1)

Glucose and/or a phosphorylated product thereof: ADP-dependent glucokinase (EC 2.7.1.147)

In a case where the measurement target is the precursor, examples of each combination of the measurement target, the kinase and the kinase forward reaction substrate and/or the phosphorylated product thereof include, but are not limited to, the followings. It is noted that each of the following combinations is described as a measurement target: a kinase: a kinase forward reaction substrate and/or the phosphorylated product thereof in this order.

Creatinine: creatine kinase: creatine and/or a phosphorylated product thereof

Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate, or 2,3-bisphosphoglycerate: 3-phosphoglycerate kinase: 3-phosphoglycerate and/or a phosphorylated product thereof Glucose-6-phosphate: phosphofructo-1-kinase: phosphofructose-6-phosphate and/or a phosphorylated product thereof Dihydroxyacetone phosphate, triglyceride, lysophosphatidylcholine, lysophosphatidate, glycerol-3-phosphate, lysophosphatidylglycerol, or phosphatidylglycerol: glycerokinase: glycerol and/or a phosphorylated product thereof Glucose-1-phosphate: ADP-dependent glucokinase: glucose and/or a phosphorylated product thereof Preferable examples include, but are not limited to, the following combinations each including a kinase specified by EC number.

Creatinine: creatine kinase (EC 2.7.3.2): creatine and/or a phosphorylated product thereof Glyceraldehyde-3-phosphate, hydroxyacetone phosphate, glycerol-3-phosphate, lysophosphatidate, lysophosphatidylcholine, fructose-1,6-bisphosphate, 2-phosphoglycerate, phosphoenolpyruvate, or 2,3-bisphosphoglycerate: 3-phosphoglycerate kinase (EC 2.7.2.3): 3-phosphoglycerate and/or a phosphorylated product thereof Glucose-6-phosphate: phosphofructo-1-kinase (EC 2.7.1.11): phosphofructose-6-phosphate and/or a phosphorylated product thereof), (hydroxyacetone phosphate, triglyceride, lysophosphatidylcholine, lysophosphatidate, glycerol-3-phosphate, lysophosphatidylglycerol, or phosphatidylglycerol: glycerokinase (EC 2.7.1.30): glycerol and/or a phosphorylated product thereof Glucose-1-phosphate: ADP-dependent glucokinase (EC 2.7.1.147): glucose and/or a phosphorylated product thereof An example of a more preferable combination of the measurement target, the kinase, and the kinase forward reaction substrate and/or the phosphorylated product thereof includes the following:

Creatinine: creatine kinase: creatine and/or a phosphorylated product thereof

In the composition according to the present embodiment, in a case where the measurement target is the kinase forward reaction substrate and/or the phosphorylated product thereof, each combination of the measurement target and the kinase can be determined in the same manner as described above with respect to the method of the present embodiment. Further, also if the measurement target is the precursor, each combination of the measurement target, the kinase, and the kinase forward reaction substrate and/or the phosphorylated product thereof can be determined in the same manner as described above with respect to the method of the present embodiment.

The first nucleotide coenzyme and the second nucleotide coenzyme are nucleotide coenzymes having different nucleoside moieties from each other. The type of the nucleoside moiety is not especially limited, and examples include adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine. Further, phosphorylated products of these may be a monophosphorylated product, a diphosphorylated product or a triphosphorylated product.

Specific examples of the nucleotide coenzymes include, but are not limited to, ATP, ADP, AMP, GTP, GDP, GMP, TTP, TDP, TMP, UTP, UDP, UMP, CTP, CDP, CMP, XTP, XDP, XMP, ITP, IDP, IMP, dATP, dADP, dAMP, dGTP, dGDP, dGMP, dTTP, dTDP, dTMP, dUTP, dUDP, dUMP, dCTP, dCDP, dCMP, dXTP, dXDP, dXMP, dITP, dIDP and dIMP. Preferable examples include ATP, ADP, GTP, GDP, TTP, TDP, UTP, UDP, CTP, CDP, XTP, XDP, ITP, IDP, dATP, dADP, dGTP, dGDP, dTTP, dTDP, dUTP, dUDP, dCTP, dCDP, dXTP, dXDP, dITP and dIDP. To such a nucleotide enzyme, for example, a substituent having coloring ability or the like may be bonded in some cases.

The nucleoside moiety of the first nucleotide coenzyme for the forward reaction used in the composition of the present embodiment is not especially limited, and examples include adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine. Preferable examples include adenosine, inosine, guanosine, deoxyadenosine and deoxyadenosine. A more preferable example includes adenosine. Besides, the phosphorylated products of these may be a monophosphorylated product, a diphosphorylated product or a triphosphorylated product, and a triphosphorylated product is preferred. Specific examples of the first nucleotide coenzyme include the aforementioned specific examples, and further preferable examples include ATP, GTP, TTP, UTP, CTP, XTP, ITP, dATP, dGTP, dTTP, dUTP, dCTP, dXTP and dITP.

The nucleoside moiety of the second nucleotide coenzyme for the reverse reaction used in the composition of the present embodiment is not especially limited, and examples include adenosine, guanosine, thymidine, uridine, cytidine, xanthosine, inosine, deoxyadenosine, deoxyguanosine, deoxythymidine, deoxyuridine, deoxycytidine, deoxyxanthosine and deoxyinosine. Preferable examples include inosine, guanosine, adenosine and deoxyguanosine. A more preferable example includes inosine. Besides, the phosphorylated products of these may be a monophosphorylated product, a diphosphorylated product or a triphosphorylated product, and a diphosphorylated product is preferred. Specific examples of the second nucleotide coenzyme include the aforementioned specific examples, and further preferable examples include ADP, GDP, TDP, UDP, CDP, XDP, IDP, dADP, dGDP, dTDP, dUDP, dCDP, dXDP and dIDP.

Combinations of the nucleoside moieties of the first nucleotide coenzyme and the second nucleotide coenzyme in the composition of the present embodiment are not especially limited as long as the nucleoside moieties are different from each other, and examples include combinations of adenosine and inosine, guanosine and adenosine, deoxyadenosine and guanosine, deoxyadenosine and deoxyguanosine, deoxyadenosine and inosine, or inosine and adenosine. Preferably, the nucleoside moiety of the first nucleotide coenzyme is adenosine, and the nucleoside moiety of the second nucleotide coenzyme is inosine.

By using the composition according to the present embodiment, for example, the method of the present embodiment can be performed, and the reaction of the formula (3) can be caused by the cycling method.

By using the composition according to the present embodiment, an amount of change of a signal corresponding to a change of any one of the first nucleotide coenzyme, the conversion product of the first nucleotide coenzyme resulting from the forward reaction, the second nucleotide coenzyme, and the conversion product of the second nucleotide coenzyme resulting from the reverse reaction can be detected. Besides, the change of the signal may be a decreased amount of the first nucleotide coenzyme or the second nucleotide coenzyme, or an increased amount of the conversion product of the first nucleotide coenzyme resulting from the forward reaction or the conversion product of the second nucleotide coenzyme resulting from the reverse reaction. Preferably, the change of the signal is the increased amount of the conversion product of the first nucleotide coenzyme resulting from the forward reaction or the conversion product of the second nucleotide coenzyme resulting from the reverse reaction. As a method for detecting the change, any of known methods such as the HPLC can be employed. In a case where the HPLC is employed, it is performed in the same manner as described with respect to the method of the present embodiment.

By using the composition according to the present embodiment, the amount, contained in a sample, of the kinase forward reaction substrate and/or the phosphorylated product thereof, or the precursor thereof can be calculated.

A calculation method is the same as that described with respect to the method of the present embodiment, and can be performed by employing a known method.

The composition according to the present embodiment may optionally contain a detection enzyme able to utilize the conversion product of the first nucleotide coenzyme resulting from the forward reaction but unable to utilize the second nucleotide coenzyme, or a detection enzyme unable to utilize the first nucleotide coenzyme but able to utilize the conversion product of the second nucleotide coenzyme resulting from the reverse reaction. An example of the detection enzyme includes, but is not limited to, adenosine diphosphate-dependent glucokinase (EC 2.7.1.147). In addition, a coenzyme of any one of thio-NADP, thio-NAD, NADP and NAD, glucose and glucose-6-phosphate dehydrogenase are added to the composition of the present embodiment in some cases. By using them, a change of any signal corresponding to the increased amount of the conversion product of the first nucleotide coenzyme resulting from the forward reaction or the conversion product of the second nucleotide coenzyme resulting from the reverse reaction can be detected and measured. Specific description is the same as that made with respect to the method of the present embodiment.

The composition according to the present embodiment may be provided as a reagent kit divided into a plurality of parts. For example, a composition containing the second nucleotide coenzyme can be distributed in a reagent kit appropriately divided into two, three or more parts. In this case, a composition containing a detection enzyme able to utilize, for example, thio-NADP, thio-NAD, NADP or NAD, glucose, and the conversion product of the first nucleotide coenzyme resulting from the forward reaction but unable to utilize the second nucleotide coenzyme, or a detection enzyme unable to utilize the first nucleotide coenzyme but able to utilize the conversion product of the second nucleotide coenzyme resulting from the reverse reaction can be distributed in the reagent kit appropriately divided into two, three or more parts. All of these components can be contained dually in some of the divided parts of the reagent kit respectively.

In a case where CK is preferably used, a composition containing ATP, CK and IDP can be appropriately divided into two parts of the reagent kit. Further, NADP, ADP-dependent glucokinase and glucose-6-phosphate dehydrogenase may be appropriately distributed to two divided parts of the reagent kit. All of these components can be contained dually in some of the divided parts of the regent kit respectively.

Now, the present invention will be further specifically described with reference to examples, and it is noted that the present invention is not limited to the following examples.

(Confirmation of Nucleotide Specificity of ADP-HK)

It was confirmed that ADP-dependent hexokinase (ADP-HKPII (T-92), Asahi Kasei Pharma Corporation) derived from *Pyrococcus furiosus* can utilize, as a phosphate donor, merely ADP but cannot utilize IDP and GDP among nucleoside diphosphates. Specifically, glucose produced by an ADP-HKPII reaction is caused to coexist with glucose-6-phosphate dehydrogenase (G6PDH: Toyobo Co., Ltd.) in the presence of NADP, so as to be measured at 37° C. as a change of an absorbance at 340 nm based on reduced NADP.

A reaction solution having the following composition was prepared:
  50 mmol/L of Tris-HCl pH 8.0
  10 mmol/L of glucose
  2 mmol/L of magnesium chloride ($MgCl_2$)

1 mmol/L of NADP
1 u/mL of G6PDH
1 mmol/L of nucleoside diphosphate (ADP, IDP or GDP)

As a reagent blank, one containing saline instead of a nucleoside diphosphate was used.

First, when ADP-HKPII was added to a concentration of 1.25 u/mL in the reaction solution, the change of the absorbance per minute was 110.4, −0.2 and −0.1 (all expressed as absorbance×1000) respectively in using ADP, IDP and GDP, and thus, the change in the absorbance was hardly observed using IDP and GDP. Next, the enzyme was added in a 80-fold amount, namely; to a concentration of 100 u/mL in the reaction solution. In using ADP, the absorbance was immediately increased beyond 3000 (absorbance×1000) but in using IDP or GDP, the change of the absorbance caused in nine minutes was respectively 4.8 and 0.7 (absorbance×1000), and thus, it was confirmed that ADP-HKII substantially does not utilize IDP and GTP as a phosphate donor.

Example 1: Confirmation Whether or not Reversible Reaction Proceeds in Coexistence of ATP and IDP Since it was confirmed that ADP-HKII substantially does not utilize IDP as a hydrogen donor, ATP was selected as a nucleoside triphosphate corresponding to the first nucleotide coenzyme, IDP was selected as a nucleoside diphosphate corresponding to the second nucleotide coenzyme, and it was examined whether or not a CK reaction proceeded in the presence of these.

A reaction solution having the following composition was prepared:
50 mmol/L of PIPES buffer (pH 7.0)
10 mmol/L of MgCl$_2$
10 mmol/L of glucose
1 mmol/L of ADP
1 mmol/L of IDP
1 mmol/L of NADP
8 mmol/L of N-acetylcysteine (NAC)
1 u/mL of G6PDH
1 u/mL of ADP-HKII One mL of the reaction solution was heated to 37° C. After adding creatine phosphate thereto to a concentration of 0.05 mmol/L in the reaction solution, CK (derived from rabbit muscle, manufactured by Oriental Yeast Co., Ltd.) was added to a concentration of 10 u/mL, and the resultant was observed to find whether or not an absorbance at 340 nm at 37° C. was to change. As a result, it was confirmed that the absorbance based on production of reduced NAD was increased with time. This reveals that both the following reactions were continuously caused to proceed by the CK:

Creatine phosphate+IDP→creatine+ITP
Creatine+ATP→creatine+ADP

Example 2: Quantitative Determination of Creatine

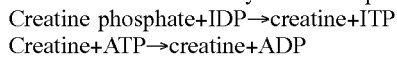

A reaction solution having the following composition was prepared:
50 mmol/L of PIPES buffer (pH 7.0)
10 mmol/L of MgCl$_2$
10 mmol/L of glucose
2 mmol/L of ATP
1 mmol/L of IDP
1 mmol/L of NADP
8 mmol/L of N-acetylcysteine (NAC)
1 u/mL of G6PDH
1 u/mL of ADP-HKII To 1 mL of the reaction solution, CK (manufactured by Asahi Kasei Pharma Corporation, HC-CKII, Catalog No. T-74) was added to a concentration of 100 u/mL. The resultant was preheated at 37° C., and when 0.05 mL of a 0 mmol/L, 0.2 mmol/L, 0.4 mmol/L or 1.2 mmol/L creatine solution was added thereto, an absorbance at 340 nm was increased in proportion to time. Therefore, the absorbance change at 340 nm from minute 3 to minute 5 was recorded. The result is illustrated in FIG. 1. As is obvious from FIG. 1, the absorbance change was in proportion to the creatine concentration in the sample.

Example 3: Rabbit, Combination of Coenzymes

A reaction solution having the following composition was prepared:
50 mmol/L of PIPES buffer (pH 7.0)
10 mmol/L of MgCl$_2$
10 mmol/L of glucose
1 mmol/L of NADP
1 mmol/L of nucleoside triphosphate
4 mmol/L of nucleoside diphosphate
8 mmol/L of N-acetylcysteine (NAC)
1 u/mL of G6PDH
1 u/mL of ADP-HKII
100 u/mL of CK (derived from rabbit muscle)

In the reaction solution, as a combination of nucleoside triphosphate (1 mmol/L) and nucleoside diphosphate (4 mmol/L), combinations of dATP/IDP, dATP/GDP, and dATP/dGDP were selected, and with respect to each of the combinations, a difference between an increased amount of the absorbance obtained by adding 0.05 mL of 0.1 mmol/L creatine and an increased amount of the absorbance obtained by adding purified water instead of the creatine was obtained. The absorbance change (absorbance×10$^3$) caused in five minutes was respectively 34.6 (dATP/IDP), 11.2 (dATP/GDP) and 8.7 (dATP/dGDP), and although there was thus a difference in extent, it was confirmed that the reaction proceeds in employing any of the combinations.

Example 4: Measurement of Creatine

A reaction solution having the following composition was prepared:
50 mmol/L PIPES buffer (pH 7.0)
10 mmol/L of MgCl$_2$
10 mmol/L of glucose
1 mmol/L of NAD
1 mmol/L of ATP
4 mmol/L of IDP
8 mmol/L of N-acetylcysteine (NAC)
1 u/mL of G6PDH
1 u/mL of ADP-HKII
250 u/mL of CK (derived from rabbit muscle)

Figure 2:
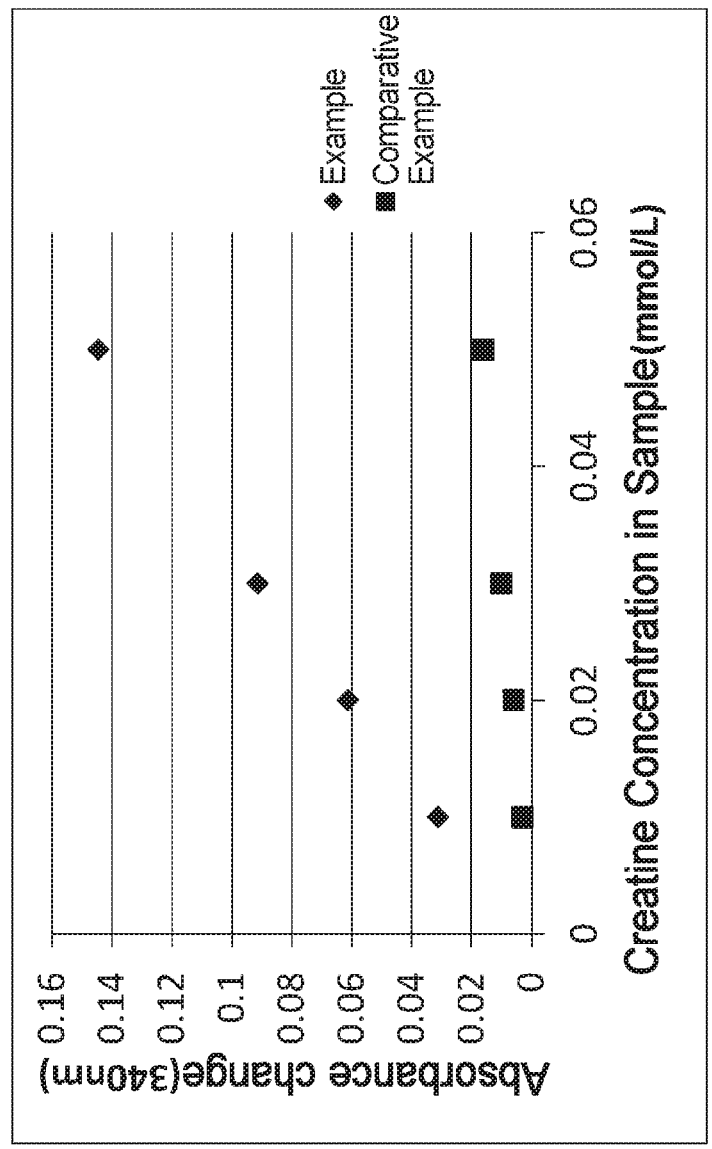
FIG. 2 is a graph illustrating the correlation between a creatine concentration in a sample and an absorbance change obtained by using a creatine kinase in an example in which deoxyinosine diphosphate (IDP) was contained in a reaction solution and in a comparative example in which IDP was not contained in a reaction solution.

To 1 mL of the reaction solution, 0.05 mL of a 0 mmol/L, 0.01 mmol/L, 0.02 mmol/L, 0.03 mmol/L or 0.05 mmol/L creatine aqueous solution was added, and the resultant was monitored for a change of an absorbance at 340 nm at 37° C. As a comparative example, a solution obtained by removing IDP from the above-described reaction solution was used for performing similar measurement. The absorbance change was measured for five minutes in the example, and the absorbance was measured 10 minutes after starting the reaction in the comparative example, and each of the thus obtained changes was subtracted from that of a reagent blank. The results of the both examples are illustrated in FIG. 2. In the present example, the absorbance change was increased about 10 times as much as that of the comparative example.

Example 5: Quantitative Determination of Creatinine

Figure 3:
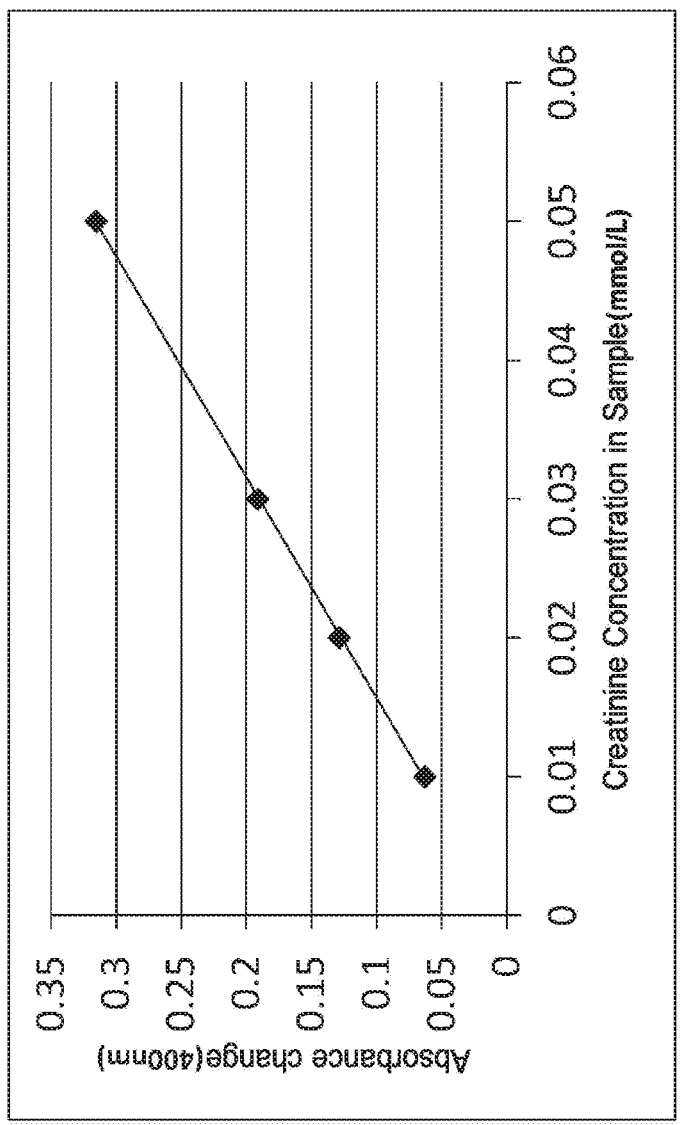
FIG. 3 is a graph illustrating the correlation between a creatinine concentration in a sample and an absorbance change obtained by using a creatine kinase.

A reaction solution 1 having the following composition was prepared:
50 mmol/L of PIPES-NaOH buffer (pH 7.0)
12 mmol/L of $MgCl_2$
10 mmol/L of glucose
5.3 mmol/L of IDP
20 u/mL creatinine amidohydrolase (manufactured by Toyobo Co., Ltd.)
In addition, a reaction solution 2 having the following composition was prepared:
200 mmol/L of PIPES buffer (pH 7.0)
2 mmol/L of $MgCl_2$
4 mmol/L of thio-NAD
4 mmol/L of ATP
10 mmol/L of N-acetylcysteine (NAC)
4 u/mL of G6PDH
4 u/mL of ADP-HKII
1000 u/mL of CK (derived from rabbit muscle)
To 0.75 mL of the reaction solution 1, 0.05 mL of a 0.01 mmol/L, 0.02 mmol/L, 0.03 mmol/L or 0.05 mmol/L creatinine solution was added respectively, and the resultant was heated at 37° C. for 5 minutes. Thereafter, 0.25 mL of the reaction solution 2 was added thereto, and an absorbance at 400 nm was monitored. An absorbance change caused from minute 2 to minute 7 after the addition of the reaction solution 2 was measured. As a result, as illustrated in FIG. 3, the absorbance change was quantitatively increased in accordance with the concentration of creatinine.

Example 6: Quantitative Determination of 3-Phosphoglycerate

Figure 4:
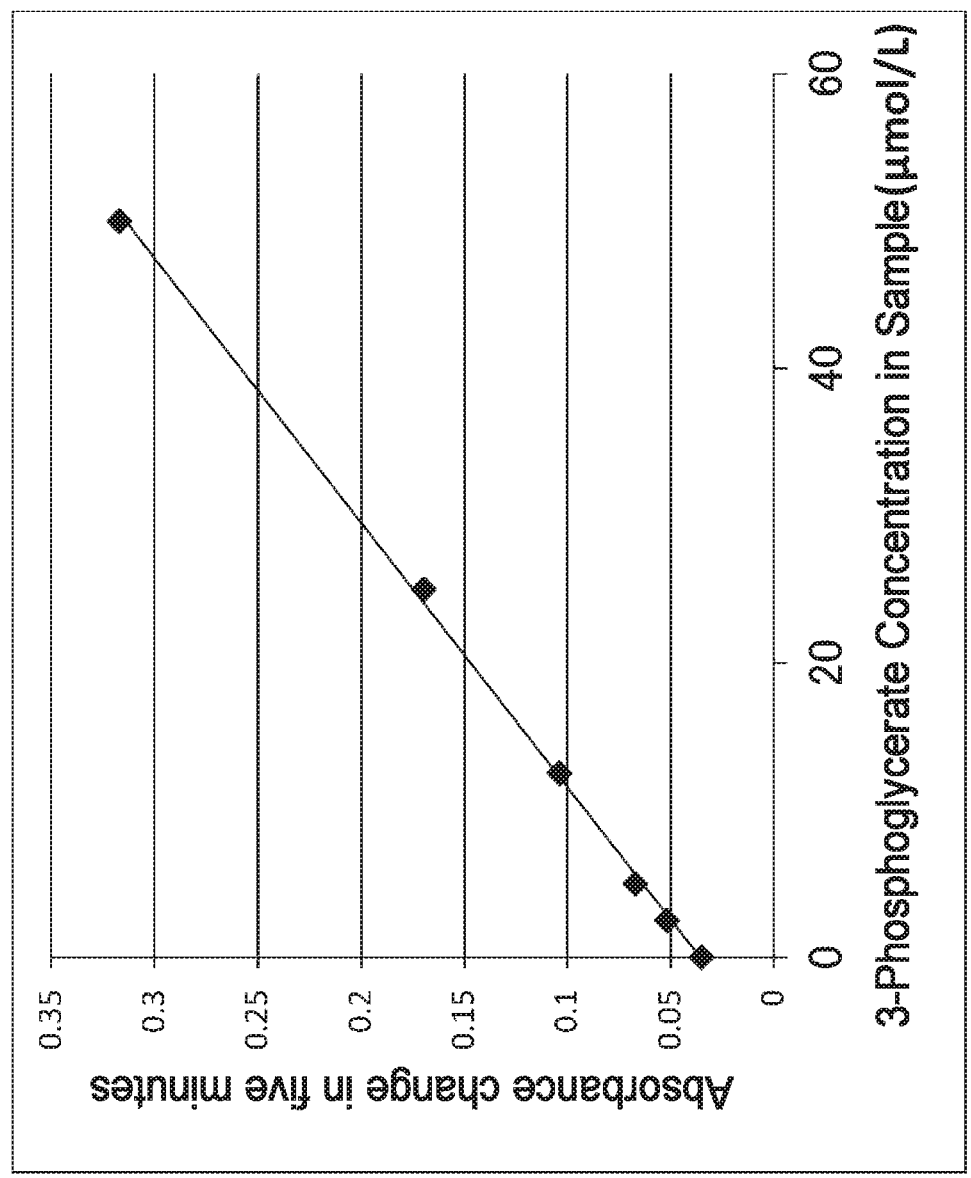
FIG. 4 is a graph illustrating the correlation between a 3-phosphoglycerate concentration in a sample and an absorbance change obtained by using a 3-phosphoglycerate kinase.

A reaction solution having the following composition was prepared:
50 mmol/L of PIPES-NaOH buffer (pH 7.5)
10 mmol/L of $MgCl_2$
10 mmol/L of glucose
1 mmol/L of ADP-HKPII
1 u/mL of G6PDH
2 mmol/L of NAD
1 mmol/L of ATP
4 mmol/L of IDP
20 u/mL of 3-phosphoglycerate kinase (PGK) (manufactured by Sigma: derived from yeast)
To 1 mL of the reaction solution, 0.02 mL of a 0 mmol/L, 0.0025 mmol/L, 0.005 mmol/L, 0.0125 mmol/L, 0.025 mmol/L or 0.05 mmol/L 3-phosphoglycerate aqueous solution was added, and an absorbance change at 340 nm at 37° C. caused from minute 1 to minute 6 after the addition of 3-phosphoglycerate was measured. The result is illustrated in FIG. 4. For comparison, in a normal measurement system where IDP was excluded from the reaction solution, an absorbance obtained by using a 50 μmol/L 3-phosphorglycerate aqueous solution was 0.006. In consideration of the molecular extinction coefficient of reduced NAD, the absorbance change caused in this example was 0.3, which was about 50 times as large as that of the normal measurement system.

Example 7: Quantitative Determination of Fructose-6-Phosphate Using Phosphofructo-1-Kinase (PFK)

Figure 5:
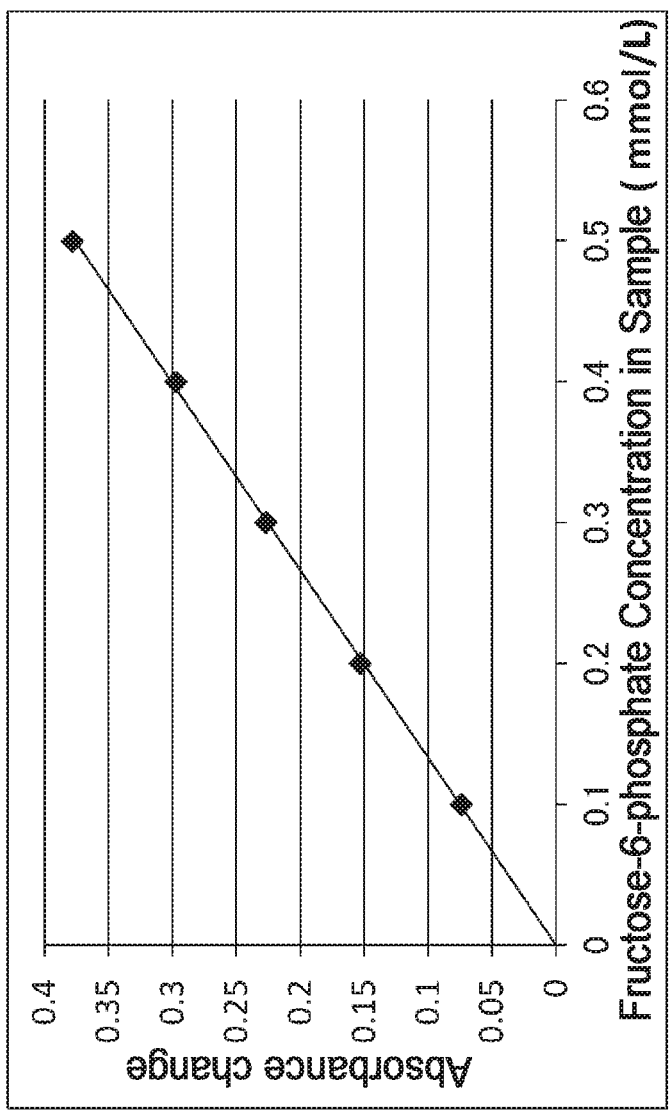
FIG. 5 is a graph illustrating the correlation between a fructose-6-phosphate concentration in a sample and an absorbance change obtained by using a phosphofructo-1-kinase.

A reaction solution having the following composition was prepared:
50 mmol/L of PIPES-NaOH buffer (pH 7.5)
5 mmol/L of $MgCl_2$
10 mmol/L of glucose
1 mmol/L of ADP-HKPII
1 u/mL of G6PDH
1 mmol/L of NAD
0.5 mmol/L of ATP
5 mmol/L of IDP
To 1 mL of the reaction solution, 0.02 mL of a 0 mmol/L, 0.1 mmol/L, 0.2 mmol/L, 0.3 mmol/L, 0.4 mmol/L or 0.5 mmol/L fructose-6-phosphate solution was added, and the resultant was preheated at 37° C. To each of the thus obtained samples, phosphofructo-1-kinase (Asahi Kasei Pharma Corporation, T-142: derived from *Geobacillus stearothermophilus*) was added to a concentration of 30 u/mL, and the reaction was started at 37° C. An absorbance change at 340 nm caused from minute 1 to minute 6 after the addition of phosphofructo-1-kinase was measured. The result is illustrated in FIG. 5. As illustrated in FIG. 5, the absorbance change was quantitatively increased in accordance with the concentration of fructose-6-phosphate.

Example 8: Quantitative Determination of Glycerol by Using GK

Figure 6:
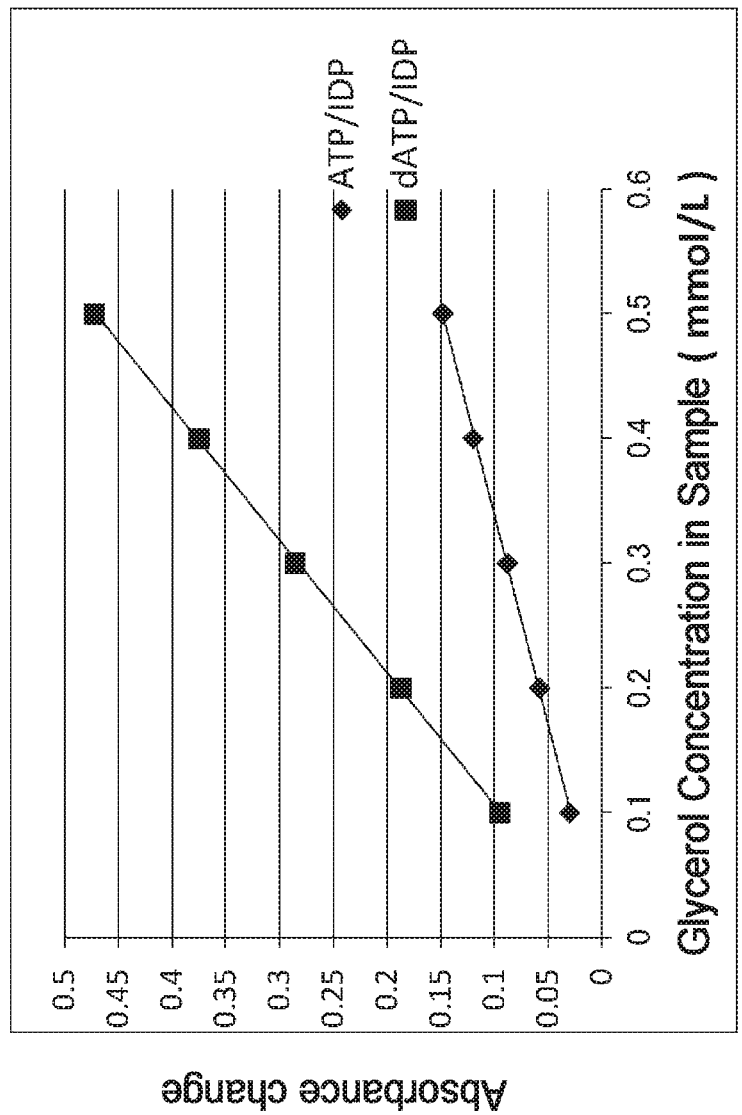
FIG. 6 is a graph illustrating the correlation between a glycerol concentration in a sample and an absorbance change obtained by using a glycerokinase.

A reaction solution having the following composition was prepared. As a glycerol kinase, an enzyme derived from microorganism was used as follows.
50 mmol/L of PIPES-NaOH buffer (pH 7.5)
5 mmol/L of $MgCl_2$
10 mmol/L of glucose
1 mmol/L of ADP-HKPII
1 u/mL of G6PDH
1 mmol/L of NAD
0.5 mmol/L of ATP
4 mmol/L of IDP
20 u/mL of Glycerol kinase (Asahi Kasei Pharma Corporation, T-64: derived from *Flavobacterium meningosepticum*)
One mL of the reaction solution was preheated, and then to the resultant, 0.02 mL of a 0 mmol/L, 0.1 mmol/L, 0.2 mmol/L, 0.3 mmol/L, 0.4 mmol/L or 0.5 mmol/L glycerol solution was added, and the reaction was started at 37° C. An absorbance change at 340 nm caused from minute 1 to minute 6 after the addition of the glycerol solution was measured. Next, with ATP replaced by deoxy-ATP, similar measurement was performed. The results are illustrated in FIG. 6. The combination of dATP and IDP attained sensitivity about three times as high as that obtained by the combination of ATP and IDP.

Example 9: PK, Effects of Addition of IDP

A reaction solution having the following composition was prepared by using pyruvate kinase derived from rabbit muscle:
50 mmol/L of PIPES-NaOH buffer (pH 7.5)
5 mmol/L of magnesium chloride ($MgCl_2$)
10 mmol/L of glucose
1 mmol/L of ADP-HKPII
1 u/mL of G6PDH 1 mmol/L of NAD
3 mmol/L of ATP
10 u/mL of pyruvate kinase (PK, Sigma, derived from rabbit muscle)

Figure 7:
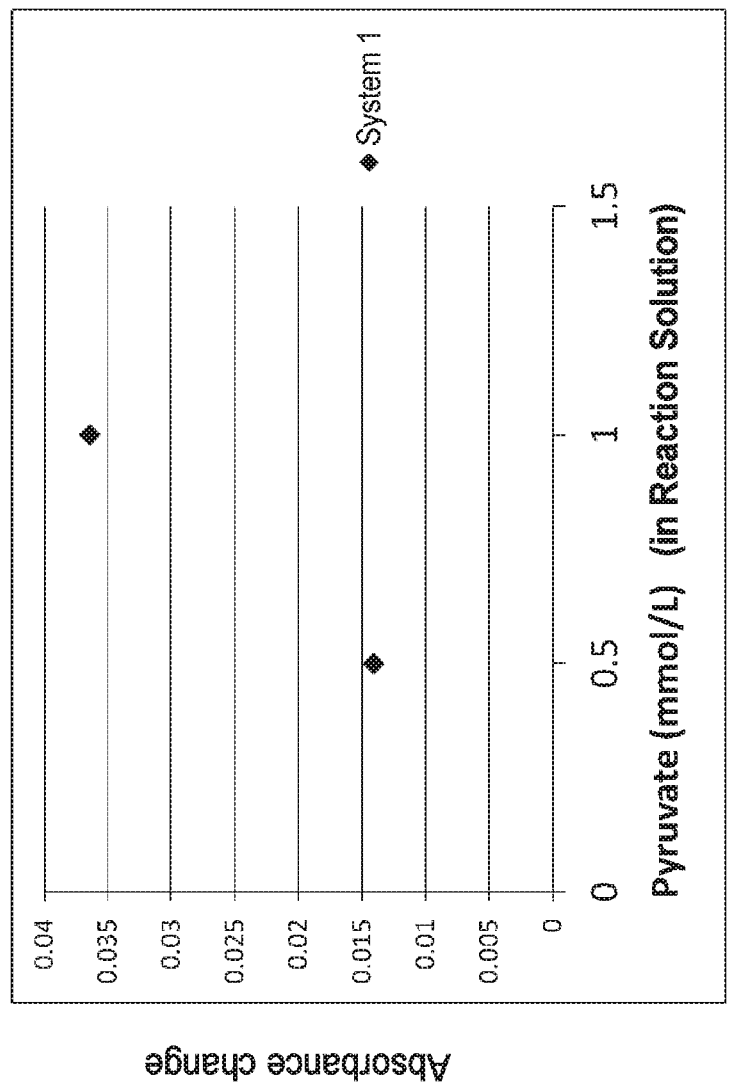
FIG. 7 is a graph illustrating the correlation between a pyruvate concentration in a sample and an absorbance change obtained by using a pyruvate kinase.

To 1 mL of the reaction solution, pyruvate was added to a concentration of 0.5 mmol/L, and the resultant was monitored for an absorbance at 340 nm at 37° C. A similar operation was performed on 1 mmol/L of pyruvate. The absorbance at 340 nm reached reaction equilibrium and showed a constant value. Next, when 1 mmol/L of IDP was further added to the reaction solution, the absorbance was linearly increased. An absorbance change caused from minute 1 to minute 11 after the addition of IDP was measured, and the result is illustrated in FIG. 7. As illustrated in FIG. 7, quantitativeness was found. This reveals that a reversible reaction of the pyruvate kinase (PK) via ATP and IDP was occurring.

Example 10: Quantitative Determination of 3-Phosphoglycerate (Detection Reaction Using E. coli GK)

A reaction solution having the following composition was prepared:
50 mmol/L of PIPES-NaOH buffer (pH 7.0)
5 mmol/L of $MgCl_2$
10 mmol/L of glycerol
5 u/mL of peroxidase (horseradish, Sigma)
0.03% of 4-aminoantipyrine
0.02% of N-ethyl-N-(2-hydroxy-3-sulfopropyl)-3-methylaniline, sodium salt, dihydrate (TOOS, Dojindo Laboratories)
1 mmol/L of GTP
1 mmol/L of ADP
20 u/mL of L-α-glycerophosphate oxidase (Asahi Kasei Pharma Corporation, GPOSP, Catalog No. T-60)
5 u/mL of 3-phosphoglycerate kinase (PGK) (manufactured by Sigma: derived from yeast)
1 u/mL of glycerokinase (GK) (derived from E. coli, Sigma)

Figure 8:
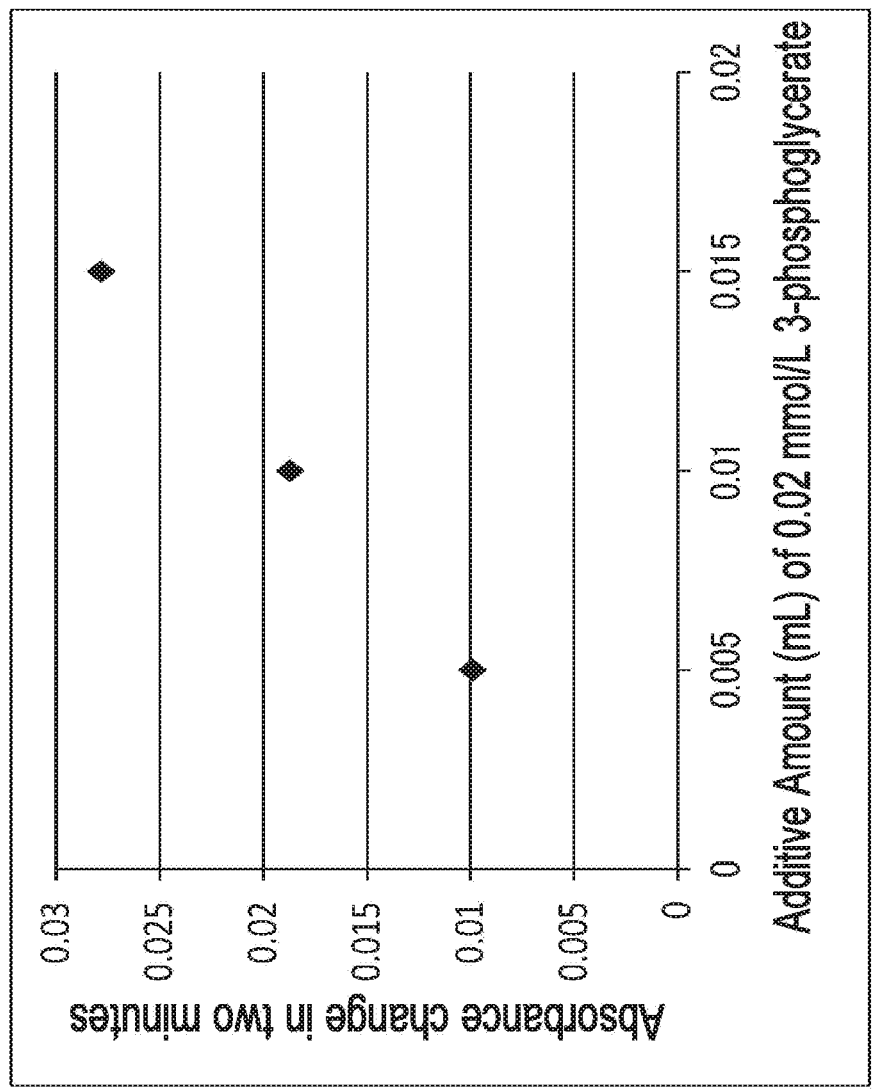
FIG. 8 is a graph illustrating the correlation between a 3-phosphoglycerate concentration in a sample and an absorbance change obtained by using a 3-phosphoglycerate kinase.

To 1 mL of the reaction solution, 0.005 mL, 0.01 mL or 0.015 mL of a 0 mmol/L or 0.02 mmol/L 3-phosphoglycerate aqueous solution was added, and the reaction was performed at 37° C. An absorbance change at 555 nm based on an oxidative condensation dye of TOOS and 4-aminoantipyrine from minute 3 to minute 5 after the addition of the 3-phosphoglycerate was measured. Although ATP and IDP were used as the nucleotide coenzymes in Example 6, a combination of GTP and ADP was selected in this example. Then, ATP thus produced was quantitatively determined by using GK derived from E. coli. With a sample to which no 3-phosphoglycerate aqueous solution was added used as a reagent blank, each result obtained by subtracting the absorbance change from that of the reagent blank is illustrated in FIG. 8. As illustrated in FIG. 8, the absorbance change was quantitatively increased in accordance with the concentration of 3-phosphoglycerate.

Example 11: Quantitative Determination of Glucose 6-Phosphate Using Hexokinase

A reaction solution having the following composition was prepared:
50 mmol/L of PIPES buffer (pH 7.0)
5 mmol/L of $MgCl_2$
0.5 mmol/L of ADP
10 mmol/L of glycerol
0.3% of 4-aminoantipyrine
20 u/mL of GPOSP (Asahi Kasei Pharma Corporation, Catalog No. T-60)
0.2% of TOOS (Dojindo Laboratories)
4.5 u/mL of peroxidase (Sigma)
1 u/mL of glycerokinase (derived from E. coli: Sigma)
50 u/mL of HKIII (Asahi Kasei Pharma Corporation, Catalog No. T-141)

Figure 9:
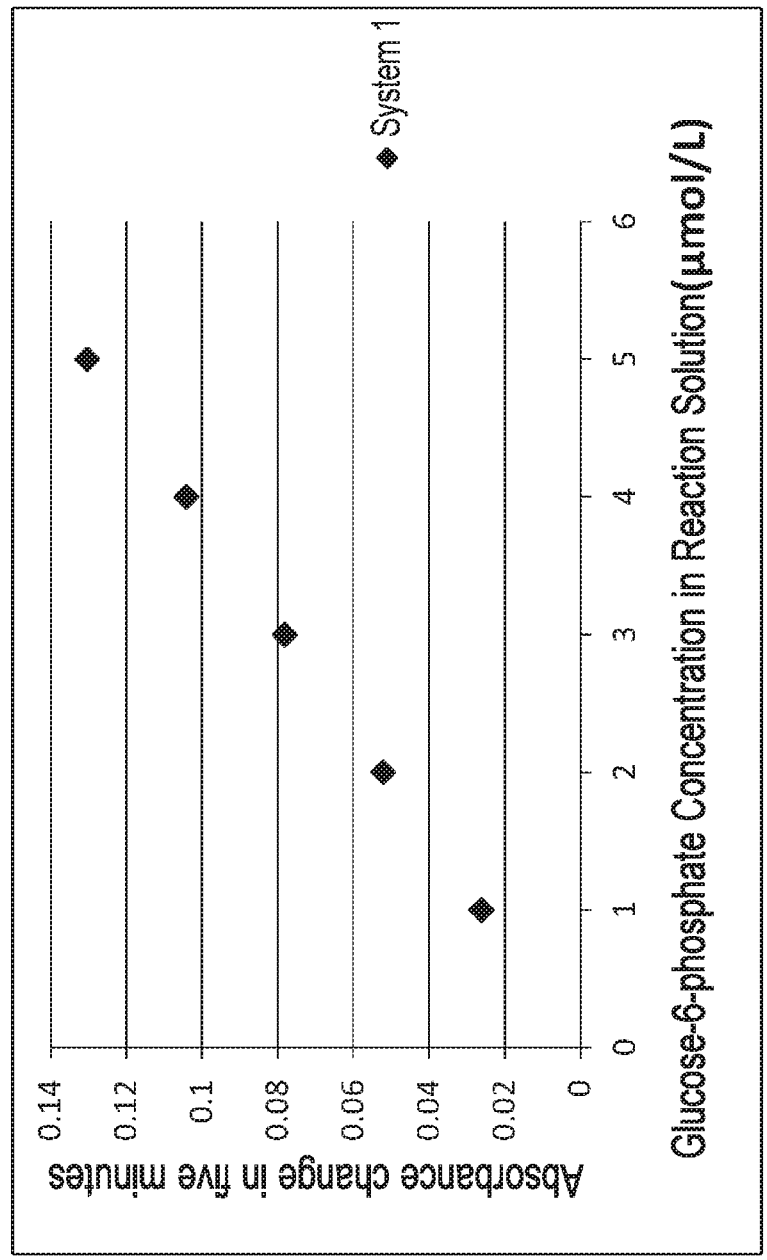
FIG. 9 is a graph illustrating the correlation between a glucose-6-phosphate concentration in a sample and an absorbance change obtained by using a hexokinase.

As the principles of the measurement, ATP produced through a HKIII reaction is specifically quantitatively determined in the coexistence of ADP and GTP using glycerokinase derived from E. coli. To 1 mL of the reaction solution, a glucose-6-phosphate solution was added to a concentration, in the reaction solution, of 1 μmol/L, 2 μmol/L, 3 μmol/L, 4 μmol/L or 5 μmol/L, and the resultant was preheated. Subsequently, a GTP aqueous solution was added thereto to a concentration, in the reaction solution, of 1 mmol/L, and the reaction was started at 37° C. An absorbance change at 555 nm caused from minute 3 to minute 8 after the addition of the GTP solution was measured. Each result of the absorbance change obtained by subtracting that of a reagent blank is illustrated in FIG. 9. As illustrated in FIG. 9, the absorbance change was quantitatively increased in accordance with the concentration of glucose-6-phosphate.

Example 12: Reverse Reaction of ADP-dependent Glucokinase

A reaction solution having the following composition was prepared:
50 mmol/L of PIPES buffer (pH 7.0)
5 mmol/L of $MgCl_2$
5 mmol/L of creatine phosphate
0.5 mmol/L of AMP
1 mmol/L of CDP
0.5 mmol/L of deamido-NAD
20 mmol/L of $NH_4Cl$
1 mmol/L of sodium cholate
0.5 u/mL of NAD synthetase (NADSII: Asahi Kasei Pharma Corporation, T-67)
2 u/mL of 12α-hydroxysteroid dehydrogenase (12α-HSDII: Asahi Kasei Pharma Corporation, T-190)
10 u/mL of CK (HC-CKII: Asahi Kasei Pharma Corporation, T-74)

Figure 10:
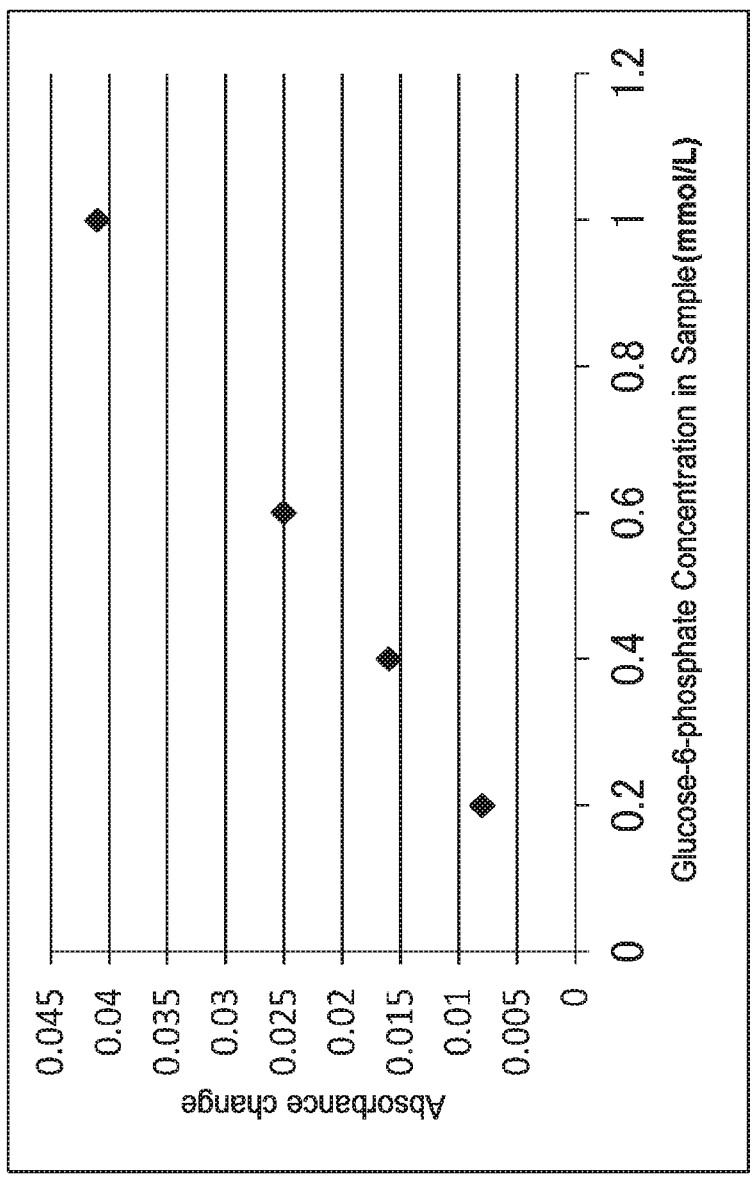
FIG. 10 is a graph illustrating the correlation between a glucose-6-phosphate concentration in a sample and an absorbance change obtained by using an adenosine diphosphate (ADP)-dependent glucokinase.

ADP-HKPII (Asahi Kasei Pharma Corporation: T-92) was used as the ADP-dependent glucokinase, and CDP and AMP were selected as the two nucleotide coenzymes. For detecting ADP produced in this example, ADP was first converted to ATP by using CK, then this ATP was converted to NAD by using the NAD synthetase, and ultimately, a rate of producing reduced NAD by 12α-HSDII was detected at 340 nm. One mL of the reaction solution was dispensed into a quartz cell, and was heated at 37° C., and then to the resultant, 0.01 mL of a 0 mmol/L, 0.2 mmol/L, 0.4 mmol/L, 0.6 mmol/L or 1 mmol/L glucose-6-phosphate solution was added, respectively. To the quartz cell in which glucose-6-phosphate at each concentration had been added, respectively, 20 u of ADP-HKPII was added, and an absorbance change at 340 nm was measured. An absorbance change caused from minute 5 to minute 7 after the addition of the enzyme was read, a result obtained in using no glucose-6-phosphate solution was subtracted as a blank, and the resultant was plotted against the concentration of the glucose-6-phosphate solution. The result is illustrated in FIG. 10. As illustrated in FIG. 10, the absorbance change was quantitatively increased in accordance with the concentration of the glucose-6-phosphate.

Example 13: Quantitative Determination of Phosphoenolpyruvate by PK

Figure 11:
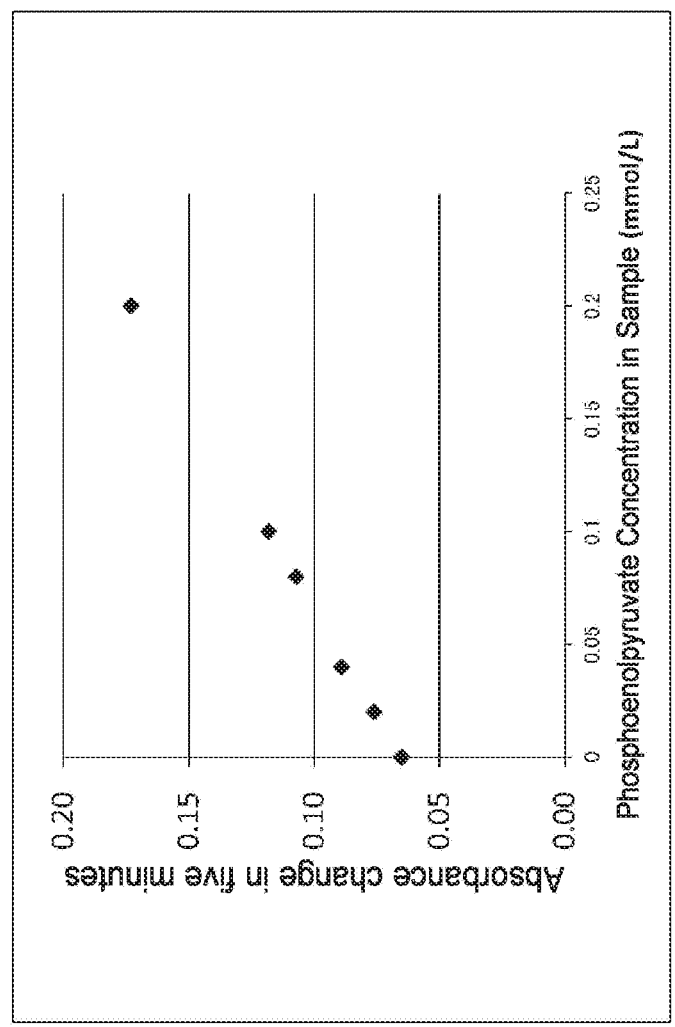
FIG. 11 is a graph illustrating the correlation between a phosphoenolpyruvate concentration in a sample and an absorbance change obtained by using a pyruvate kinase.

A reaction solution having the following composition was prepared:
50 mmol/L of Tris-HCl buffer (pH 9.0)
5 mmol/L of magnesium chloride
10 mmol/L of glucose
50 mmol/L of potassium chloride
1 u/mL of ADP-HK (manufactured by Asahi Kasei Pharma Corporation: T-92)
1 u/mL of G6PDH (manufactured by Toyobo Co., Ltd.)
1 mmol/L of NAD
2 mmol/L of ATP
50 u/mL of pyruvate kinase (PK, Sigma, derived from rabbit muscle)
To 1 mL of the reaction solution, 0.02 mL of a 0 mmol/L, 0.02 mmol/L, 0.04 mmol/L, 0.08 mmol/L, 0.1 mmol/L or 0.2 mmol/L potassium phosphoenolpyruvate aqueous solution was added, and the resultant was preheated at 37° C. Thereafter, 0.05 mL of a 10 mmol/L IDP solution was added thereto, and the reaction was started. An absorbance change at 340 nm caused minute 3 to minute 8 after the addition of IDP was measured. As a result, as illustrated in FIG. 11, the absorbance change was quantitatively increased in proportion to the concentration of the phosphoenolpyruvate.

Example 14: Quantitative Determination of Creatinine

A DNA encoding mouse B-type isozyme was obtained by a usual method. This gene was inserted, for cloning, into a host/vector system used for production of CK (manufactured by Asahi Kasei Pharma Corporation, Catalog No. T-74), so as to obtain CK-B (human-derived B-type isozyme) by a usual method.

Besides, a reaction solution 1 having the following composition was prepared:
50 mmol/L of TES buffer (pH 7.5)
12 mmol/L of magnesium chloride
12 mmol/L of glucose
1.5 u/mL of ADP-HK (manufactured by Asahi Kasei Pharma Corporation: T-92)
1.5 u/mL of G6PDH (manufactured by Toyobo Co., Ltd.)
1.5 mmol/L of thio-NAD (manufactured by Oriental Yeast Co., Ltd.)
0.7 mmol/L of ATP Furthermore, a reaction solution 2 having the following composition was prepared:
50 mmol/L of TES buffer (pH 7.5)
8 mmol/L of IDP
0.5 mmol/L of N-acetylcysteine
0.02% of BSA
16 u/mL of creatinine amidohydrolase (manufactured by Toyobo Co., Ltd.)
200 u/mL of CK-B (human-derived B-type isozyme)

Figure 12:
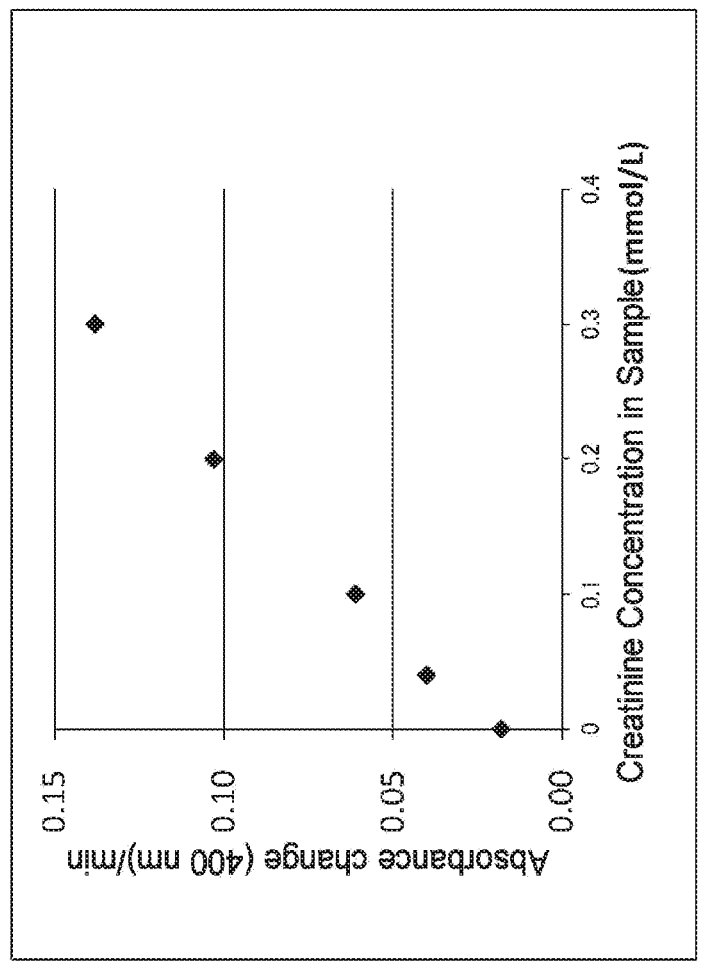
FIG. 12 is a graph illustrating the correlation between a creatinine concentration in a sample and an absorbance change obtained by using a creatine kinase.

A reaction for converting creatinine to creatine by creatinine amidohydrolase and a CK cycling reaction were simultaneously performed. To 0.75 mL of the reaction solution 1, 0.05 mL of a 0.04 mmol/L, 0.1 mmol/L, 0.2 mmol/L or 0.3 mmol/L creatinine aqueous solution was added, and the resultant was preheated for three minutes at 37° C. Subsequently, 0.25 mL of the reaction solution 2 was added thereto, and the reaction was started. An absorbance change at 400 nm caused minute 3 to minute 4 after the addition of the reaction solution 2 was measured. As a result, as illustrated in FIG. 12, the absorbance change was quantitatively increased in accordance with the concentration of the creatinine.

The invention claimed is:
1. A measuring method for at least one of creatine, creatine phosphate, and creatinine, comprising:
(1) conducting a cycling reaction according to the following Formula (1):

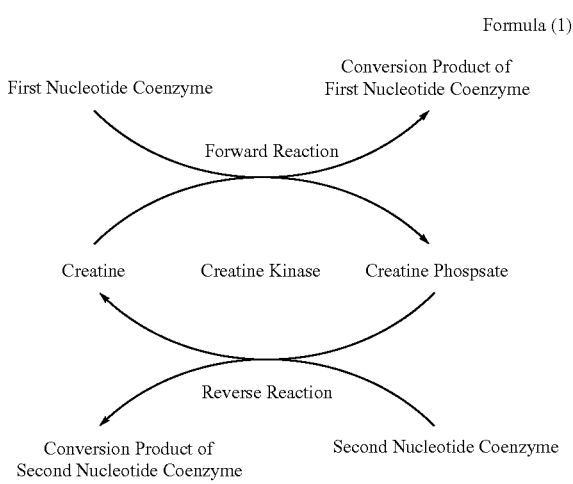

Formula (1)

by bringing:
i) a creatine kinase capable of catalyzing a forward reaction for producing the creatine phosphate from the creatine and a reverse reaction thereof in the presence of nucleotide coenzymes, the kinase being capable of utilizing nucleotide coenzymes at least having different nucleoside moieties in the forward reaction and the reverse reaction, respectively,
ii) a first nucleotide coenzyme, and
iii) a second nucleotide coenzyme having a different nucleoside moiety from the first nucleotide coenzyme
into contact with a sample or a sample having been subjected to a quantitative derivation treatment from the creatinine to the creatine and/or the creatine phosphate in a case where a measurement target is at least the creatinine;
(2) detecting an amount of change of a signal corresponding to a change of at least any one of the first nucleotide coenzyme, a conversion product of the first nucleotide coenzyme, the second nucleotide coenzyme, and a conversion product of the second nucleotide coenzyme; and
(3) calculating, on the basis of the detected change of the signal, an amount of at least one of the creatine, the creatine phosphate, and the creatinine.

2. The measuring method according to claim 1, wherein the measurement target is the creatine and/or the creatine phosphate.

3. The measuring method according to claim 1, wherein the measurement target is creatinine.

4. The measuring method according to claim 1, wherein creatinine is brought into contact with creatinine amidohydrolase (EC 3.5.2.10) in the presence of water in the quantitative derivation treatment.

5. The measuring method according to claim 1, wherein the nucleoside moiety of the first nucleotide coenzyme is any one of adenosine, guanosine, thymidine, uridine, cytidine, xanthosine, inosine, deoxyadenosine, deoxyguanosine, deoxythymidine, deoxyuridine, deoxycytidine, deoxyxanthosine, and deoxyinosine.

6. The measuring method according to claim 1, wherein the nucleoside moiety of the second nucleotide coenzyme is any one of guano sine, thymidine, uridine, cytidine, xanthosine, inosine, deoxyguanosine, deoxythymidine, deoxyuridine, deoxycytidine, deoxyxanthosine, and deoxyinosine.

7. The measuring method according to claim 1, wherein a combination of the nucleoside moiety of the first nucleotide coenzyme and the nucleoside moiety of the second nucleotide coenzyme is a combination of adenosine and inosine, deoxyadenosine and guanosine, deoxyadenosine and deoxyguanosine, or deoxyadenosine and inosine.

8. The measuring method according to claim 1, wherein the nucleoside moiety of the first nucleotide coenzyme is adenosine, and the nucleoside moiety of the second nucleotide coenzyme is inosine.

9. The measuring method according to claim 1, wherein the first nucleotide coenzyme is adenosine triphosphate (ATP), and the second nucleotide coenzyme is inosine diphosphate (IDP).

10. The measuring method according to claim 1, wherein in the detecting the change of the signal, an amount of change of a signal corresponding to an increased amount of the conversion product of the first nucleotide coenzyme resulting from the forward reaction or the conversion product of the second nucleotide coenzyme resulting from the reverse reaction is detected by using a detection enzyme able to utilize the conversion product of the first nucleotide coenzyme resulting from the forward reaction but unable to utilize the second nucleotide coenzyme, or a detection enzyme unable to utilize the first nucleotide coenzyme but able to utilize the conversion product of the second nucleotide coenzyme resulting from the reverse reaction.

11. The measuring method according to claim 1, wherein in the detecting the change of the signal, an amount of change of a signal varied in accordance with an increased amount of adenosine diphosphate (ADP) is detected by using adenosine diphosphate (ADP)-dependent glucokinase (EC 2.7.1.147) in the presence of glucose.

12. The measuring method according to claim 1, wherein in the detecting the amount of change of the signal, an amount of change of a signal varied in accordance with an increased amount of adenosine diphosphate (ADP) is detected by using adenosine diphosphate (ADP)-dependent glucokinase (EC 2.7.1.147) in the presence of glucose, glucose 6-phosphate dehydrogenase, and any one of coenzymes of thionicotinamide adenine dinucleotide phosphate (thio-NADP), thionicotinamide adenine dinucleotide (thio-NAD), nicotinamide adenine dinucleotide phosphate (NADP), and nicotinamide adenine dinucleotide (NAD).

13. The measuring method according to claim 2, wherein the nucleoside moiety of the first nucleotide coenzyme is any one of adenosine, guanosine, thymidine, uridine, cytidine, xanthosine, inosine, deoxyadenosine, deoxyguanosine, deoxythymidine, deoxyuridine, deoxycytidine, deoxyxanthosine, and deoxyinosine.

14. The measuring method according to claim 2, wherein the nucleoside moiety of the second nucleotide coenzyme is any one of guanosine, thymidine, uridine, cytidine, xanthosine, inosine, deoxyguanosine, deoxythymidine, deoxyuridine, deoxycytidine, deoxyxanthosine, and deoxyinosine.

15. The measuring method according to claim 2, wherein a combination of the nucleoside moiety of the first nucleotide coenzyme and the nucleoside moiety of the second nucleotide coenzyme is a combination of adenosine and inosine, deoxyadenosine and guanosine, deoxyadenosine and deoxyguanosine, or deoxyadenosine and inosine.

16. The measuring method according to claim 2, wherein the nucleoside moiety of the first nucleotide coenzyme is adenosine, and the nucleoside moiety of the second nucleotide coenzyme is inosine.

17. The measuring method according to claim 2, wherein in the detecting the change of the signal, an amount of change of a signal corresponding to an increased amount of the conversion product of the first nucleotide coenzyme resulting from the forward reaction or the conversion product of the second nucleotide coenzyme resulting from the reverse reaction is detected by using a detection enzyme able to utilize the conversion product of the first nucleotide coenzyme resulting from the forward reaction but unable to utilize the second nucleotide coenzyme, or a detection enzyme unable to utilize the first nucleotide coenzyme but able to utilize the conversion product of the second nucleotide coenzyme resulting from the reverse reaction.

18. The measuring method according to claim 2, wherein in the detecting the change of the signal, an amount of change of a signal varied in accordance with an increased amount of adenosine diphosphate (ADP) is detected by using adenosine diphosphate (ADP)-dependent glucokinase (EC 2.7.1.147) in the presence of glucose.

19. The measuring method according to claim 2, wherein in the detecting the amount of change of the signal, an amount of change of a signal varied in accordance with an increased amount of adenosine diphosphate (ADP) is detected by using adenosine diphosphate (ADP)-dependent glucokinase (EC 2.7.1.147) in the presence of glucose, glucose 6-phosphate dehydrogenase, and any one of coenzymes of thionicotinamide adenine dinucleotide phosphate (thio-NADP), thionicotinamide adenine dinucleotide (thio-NAD), nicotinamide adenine dinucleotide phosphate (NADP), and nicotinamide adenine dinucleotide (NAD).

20. The measuring method according to claim 3, wherein the nucleoside moiety of the first nucleotide coenzyme is any one of adenosine, guanosine, thymidine, uridine, cytidine, xanthosine, inosine, deoxyadenosine, deoxyguanosine, deoxythymidine, deoxyuridine, deoxycytidine, deoxyxanthosine, and deoxyinosine.

21. The measuring method according to claim 3, wherein the nucleoside moiety of the second nucleotide coenzyme is any one of guanosine, thymidine, uridine, cytidine, xanthosine, inosine, deoxyguanosine, deoxythymidine, deoxyuridine, deoxycytidine, deoxyxanthosine, and deoxyinosine.

22. The measuring method according to claim 3, wherein a combination of the nucleoside moiety of the first nucleotide coenzyme and the nucleoside moiety of the second nucleotide coenzyme is a combination of adenosine and inosine, deoxyadenosine and guanosine, deoxyadenosine and deoxyguanosine, or deoxyadenosine and inosine.

23. The measuring method according to claim 3, wherein the nucleoside moiety of the first nucleotide coenzyme is adenosine, and the nucleoside moiety of the second nucleotide coenzyme is inosine.

24. The measuring method according to claim 3, wherein in the detecting the change of the signal, an amount of change of a signal corresponding to an increased amount of the conversion product of the first nucleotide coenzyme resulting from the forward reaction or the conversion product of the second nucleotide coenzyme resulting from the reverse reaction is detected by using a detection enzyme able to utilize the conversion product of the first nucleotide coenzyme resulting from the forward reaction but unable to utilize the second nucleotide coenzyme, or a detection enzyme unable to utilize the first nucleotide coenzyme but able to utilize the conversion product of the second nucleotide coenzyme resulting from the reverse reaction.

25. The measuring method according to claim 3, wherein in the detecting the change of the signal, an amount of change of a signal varied in accordance with an increased amount of adenosine diphosphate (ADP) is detected by using adenosine diphosphate (ADP)-dependent glucokinase (EC 2.7.1.147) in the presence of glucose.

26. The measuring method according to claim 3, wherein in the detecting the amount of change of the signal, an amount of change of a signal varied in accordance with an increased amount of adenosine diphosphate (ADP) is detected by using adenosine diphosphate (ADP)-dependent glucokinase (EC 2.7.1.147) in the presence of glucose, glucose 6-phosphate dehydrogenase, and any one of coenzymes of thionicotinamide adenine dinucleotide phosphate (thio-NADP), thionicotinamide adenine dinucleotide (thio-NAD), nicotinamide adenine dinucleotide phosphate (NADP), and nicotinamide adenine dinucleotide (NAD).

27. The measurement method according to claim 1, wherein the forward reaction and reverse reaction occur at the same rate.

28. The measurement method according to claim 2, wherein the forward reaction and reverse reaction occur at the same rate.

29. The measurement method according to claim 3, wherein the forward reaction and reverse reaction occur at the same rate.

30. The measurement method according to claim 4, wherein the forward reaction and reverse reaction occur at the same rate.

31. The measurement method according to claim 9, wherein the forward reaction and reverse reaction occur at the same rate.

32. The measurement method according to claim 1, wherein the conducting the cycling reaction is in vitro.

33. The measurement method according to claim 2, wherein the conducting the cycling reaction is in vitro.

34. The measurement method according to claim 3, wherein the conducting the cycling reaction is in vitro.

35. The measurement method according to claim 4, wherein the conducting the cycling reaction is in vitro.

36. The measurement method according to claim 9, wherein the conducting the cycling reaction is in vitro.

* * * * *

UNITED STATES PATENT AND TRADEMARK OFFICE
CERTIFICATE OF CORRECTION

PATENT NO. : 10,472,665 B2
APPLICATION NO. : 15/510059
DATED : November 12, 2019
INVENTOR(S) : S. Ueda et al.

It is certified that error appears in the above-identified patent and that said Letters Patent is hereby corrected as shown below:

In the Claims

Column 37, Line 9, Claim 6, Line 3, please change "guano sine" to --guanosine--.

Signed and Sealed this
Second Day of June, 2020

Andrei Iancu
*Director of the United States Patent and Trademark Office*